(12) United States Patent
Chu

(10) Patent No.: US 6,936,054 B2
(45) Date of Patent: Aug. 30, 2005

(54) PLACING SUTURES

(75) Inventor: Michael S. H. Chu, Brookline, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 237 days.

(21) Appl. No.: 10/200,271

(22) Filed: Jul. 22, 2002

(65) Prior Publication Data
US 2004/0015177 A1 Jan. 22, 2004

(51) Int. Cl.⁷ .............................................. A61B 17/04
(52) U.S. Cl. ..................................... 606/145; 606/144
(58) Field of Search ................................. 606/144–145

(56) References Cited

U.S. PATENT DOCUMENTS

| | | |
|---|---|---|
| 1,822,330 A | 9/1931 | Ainslie |
| 2,738,790 A | 3/1956 | Todt, Sr. et al. |
| 3,840,017 A | 10/1974 | Violante .................... 128/340 |
| 4,651,733 A | 3/1987 | Mobin-Uddin |
| 4,957,498 A | 9/1990 | Caspari et al. .............. 606/146 |
| 5,015,250 A | 5/1991 | Foster |
| 5,059,201 A | 10/1991 | Asnis |
| 5,250,054 A | 10/1993 | Li |
| 5,312,422 A | 5/1994 | Trott |
| 5,336,239 A | 8/1994 | Gimpelson |
| 5,337,736 A | 8/1994 | Reddy |
| 5,350,385 A | 9/1994 | Christy |
| 5,364,408 A | 11/1994 | Gordon |
| 5,364,409 A | 11/1994 | Kuwabara et al. |
| 5,405,354 A | 4/1995 | Sarrett |
| 5,439,467 A | 8/1995 | Benderev et al. |
| 5,439,469 A | 8/1995 | Heaven et al. |
| 5,445,167 A | 8/1995 | Yoon et al. |
| 5,449,366 A | 9/1995 | Li |
| 5,458,609 A | 10/1995 | Gordon et al. |
| 5,468,251 A | 11/1995 | Buelna |
| 5,474,565 A | 12/1995 | Trott |
| 5,522,820 A | 6/1996 | Caspari et al. |
| 5,540,704 A | 7/1996 | Gordon et al. |
| 5,562,686 A | 10/1996 | Sauer et al. |
| 5,571,119 A | 11/1996 | Atala |
| 5,573,540 A | 11/1996 | Yoon |
| 5,578,044 A | 11/1996 | Gordon et al. |
| 5,591,179 A | 1/1997 | Edelstein .................... 606/144 |
| 5,601,578 A | 2/1997 | Murphy |
| 5,618,290 A | 4/1997 | Toy et al. ................... 606/139 |
| 5,632,752 A | 5/1997 | Buelna |
| 5,643,292 A | 7/1997 | Hart |
| 5,649,939 A | 7/1997 | Reddick |
| 5,653,717 A | 8/1997 | Ko et al. |
| 5,662,663 A | 9/1997 | Shallman .................... 606/144 |
| 5,676,675 A | 10/1997 | Grice |
| 5,697,941 A | 12/1997 | Christy |
| 5,713,908 A | 2/1998 | Jameel et al. |
| 5,713,910 A | 2/1998 | Gordon et al. |
| 5,741,277 A | 4/1998 | Gordon et al. |

(Continued)

FOREIGN PATENT DOCUMENTS

WO    WO 96/27331    9/1996

OTHER PUBLICATIONS

Copy of International Search Report for International Patent Application No. PCT/US03/22513, mailed from the International Search Authority on Nov. 25, 2003.

Primary Examiner—Gary Jackson
(74) Attorney, Agent, or Firm—Edwards & Angell, LLP

(57) ABSTRACT

A suturing instrument is configured for to apply sutures to approximate, ligate, or fixate tissue in, for example, open, mini-incision, trans-vaginal, or endoscopic surgical procedures. The suturing instrument includes an elongate body member, a needle exit port, a needle receiving port, and a needle deployment mechanism. The suturing instrument eliminates the need for a preassembled needle and suture and reduces or eliminates the possibility of needle loss during suturing.

18 Claims, 27 Drawing Sheets

U.S. PATENT DOCUMENTS

| | | |
|---|---|---|
| 5,741,301 A | 4/1998 | Pagedas |
| 5,746,753 A | 5/1998 | Sullivan et al. |
| 5,772,672 A | 6/1998 | Toy et al. |
| 5,776,148 A | 7/1998 | Christy |
| 5,860,992 A | 1/1999 | Daniel et al. |
| 5,873,876 A | 2/1999 | Christy |
| 5,908,428 A | 6/1999 | Scirica et al. ............... 606/139 |
| 5,919,199 A | 7/1999 | Mers Kelly et al. ........ 606/139 |
| 5,980,538 A * | 11/1999 | Fuchs et al. ................ 606/145 |
| 6,010,514 A | 1/2000 | Burney et al. ............... 606/144 |
| 6,048,351 A | 4/2000 | Gordon et al. |
| 6,071,292 A | 6/2000 | Makower et al. |
| 6,132,439 A | 10/2000 | Kontos |
| 6,221,084 B1 | 4/2001 | Fleenor |
| 6,258,106 B1 | 7/2001 | Leonard |
| 6,428,549 B1 | 8/2002 | Kontos ....................... 606/144 |
| 6,475,135 B1 | 11/2002 | Levy ........................... 600/30 |

* cited by examiner

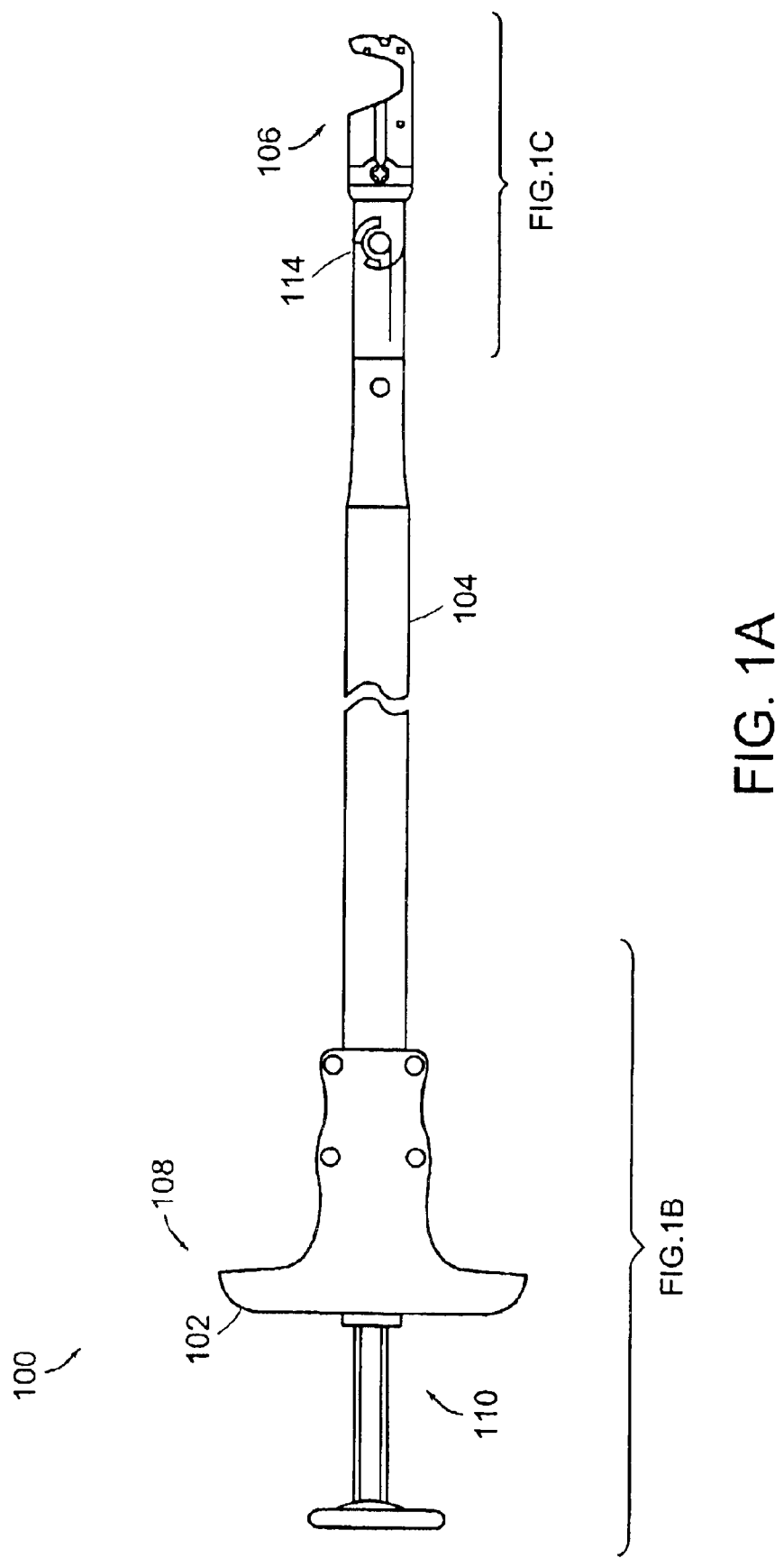

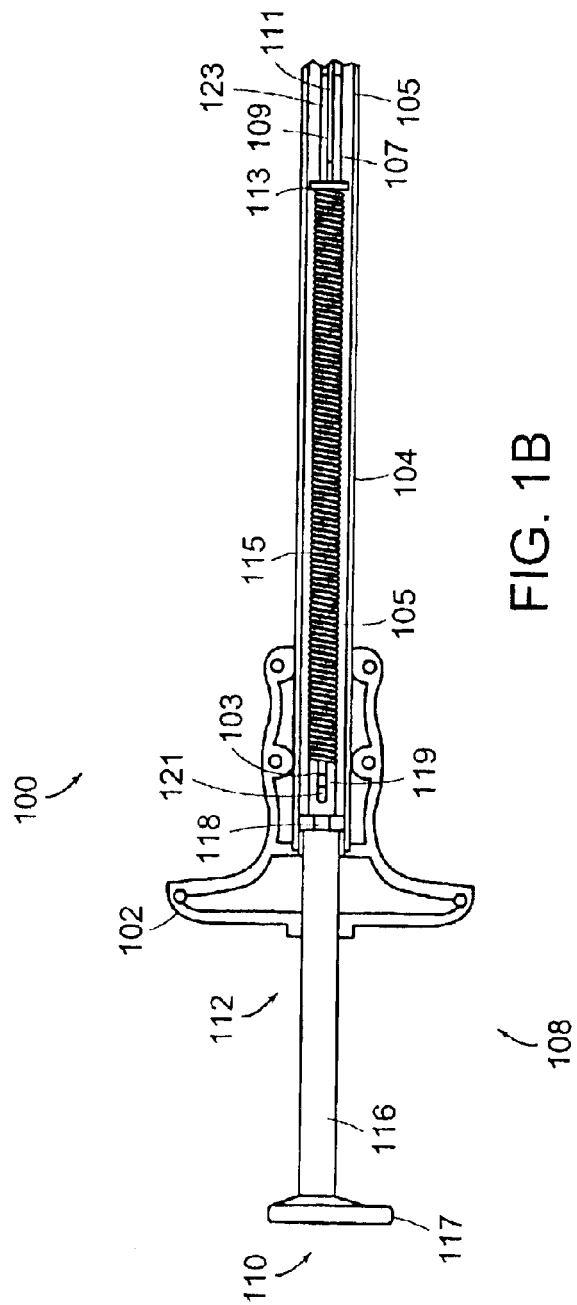
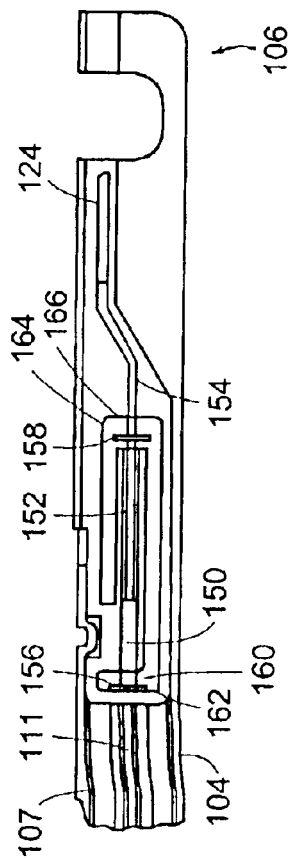
FIG. 1B
FIG. 1C

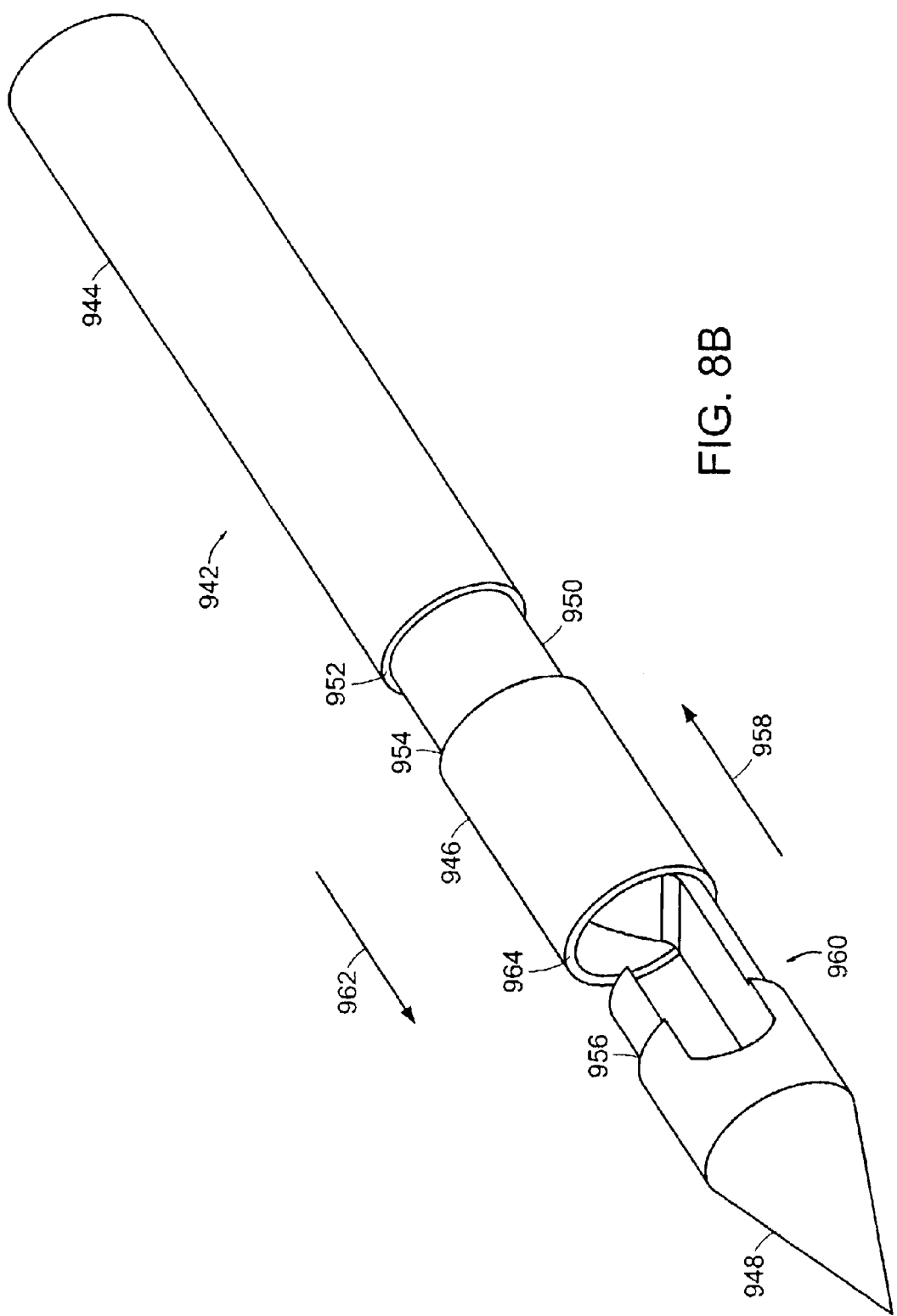

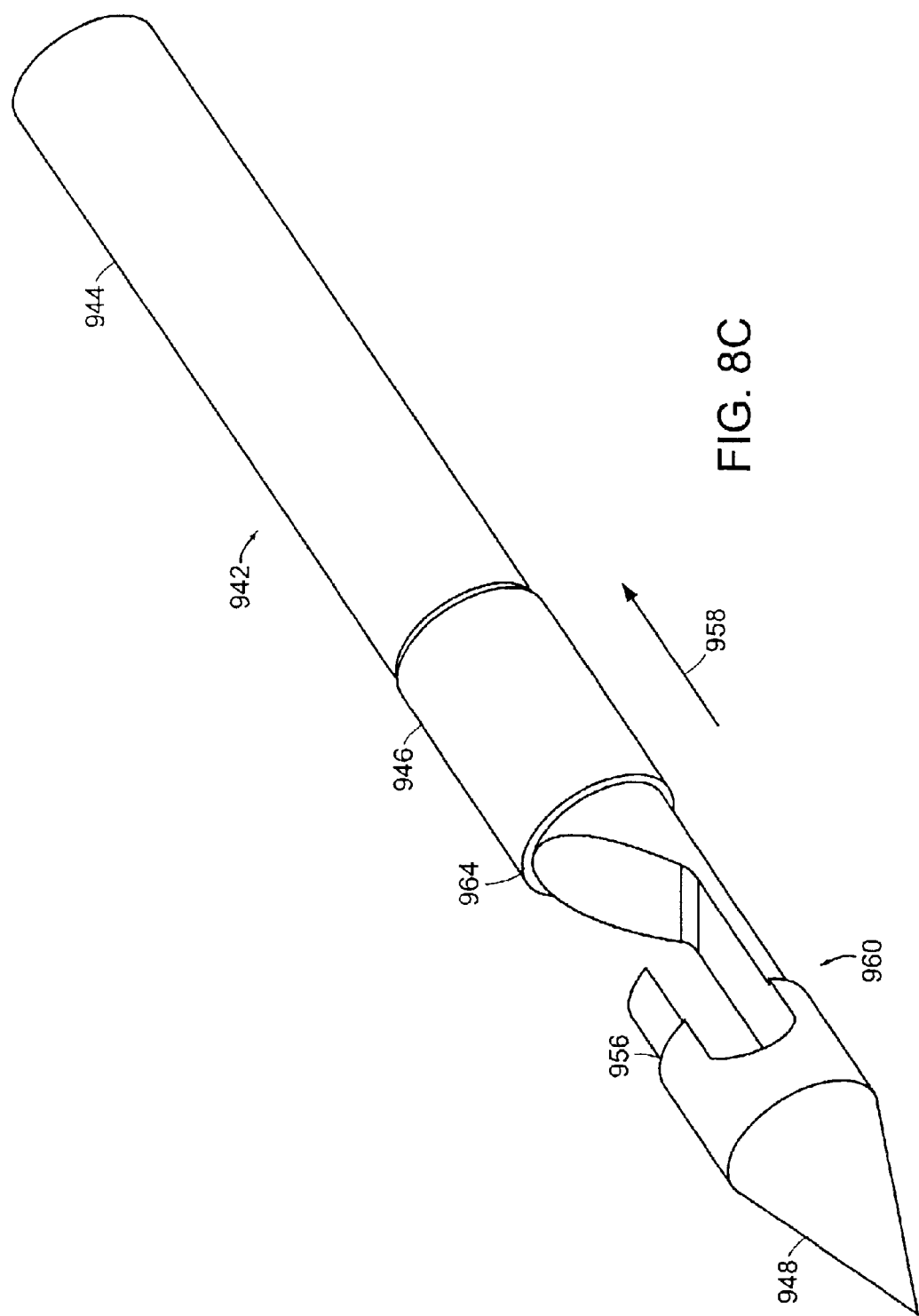

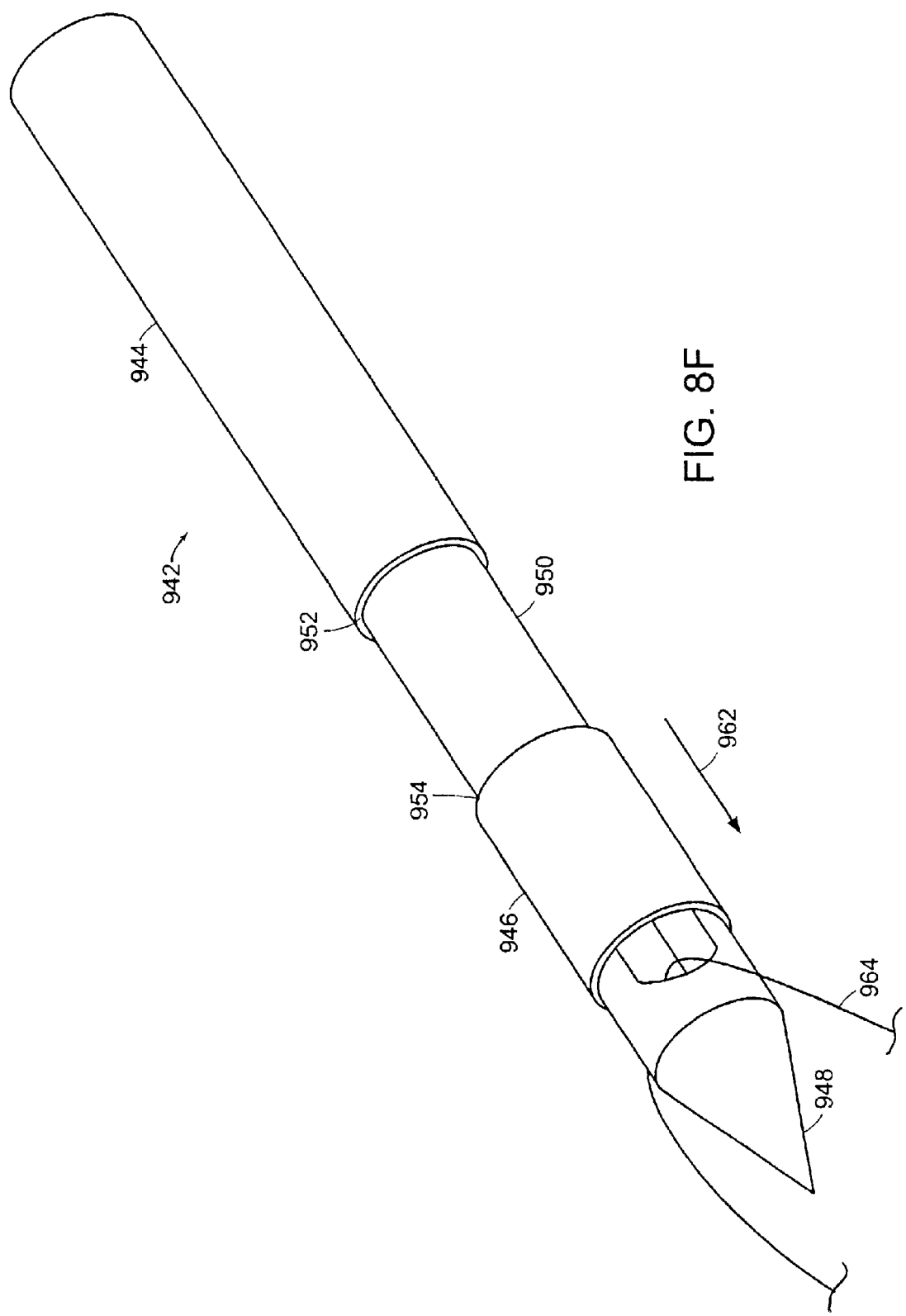

PLACING SUTURES

TECHNICAL FIELD

The invention relates to devices and methods for placing sutures.

BACKGROUND INFORMATION

Suturing of body tissue is a time consuming aspect of many surgical procedures. For many surgical procedures, it is necessary to make a large opening in the human body to expose the area that requires surgical repair. There are instruments available that allow for viewing of certain areas of the human body through a small puncture wound without exposing the entire body cavity. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

SUMMARY OF THE INVENTION

The invention generally relates to a medical device for performing a surgical procedure, such as passing a suture through tissue. Specifically, the invention relates to a suturing instrument that eliminates the need for a preassembled needle and suture and reduces or eliminates the possibility of needle loss during suturing. The suturing instrument is configured to apply sutures to approximate, ligate, or fixate tissue in, for example, open, mini-incision, trans-vaginal, or endoscopic surgical procedures.

The suturing instrument uses a needle housed within an elongate body member. The needle has a sharpened tip for tissue penetration and a hook-shaped distal portion for capturing a suture. When the suturing instrument is actuated, the needle is advanced out of the elongate body of the suturing instrument through tissue and into a second opening in the suturing instrument. The needle captures a suture held within the second opening of the suturing instrument in the hook-shaped distal portion of the needle. The needle is then retracted back through the tissue carrying the suture through the tissue. Alternatively, the needle can travel about the tissue, as opposed to through the tissue, thereby carrying the suture back around the tissue to ligate a vessel, for example. The suturing instrument can then be removed from the body leaving the suture intact.

In one aspect, the invention is directed to a suturing instrument including an elongate body member including a distal portion defining a first opening and a second opening opposing the first opening, a needle, and a needle deployment mechanism. The needle is at least partially disposed within the elongate body member and includes a hook-shaped distal portion and a tissue-penetrating tip distal of the hook-shaped distal portion. The needle deployment mechanism is coupled to a proximal portion of the needle and disposed at least partially within the elongate body member. The needle deployment mechanism moves the needle between the first and second openings. In one embodiment, the needle includes a latch movable between a first position in which the hook-shaped distal portion is open and a second position in which the hook-shaped distal portion is closed.

In another aspect, the invention relates to a suturing instrument including an elongate body member including a distal portion defining a first opening and a second opening that opposes the first opening, a needle at least partially disposed within the elongate body member, and a needle deployment mechanism coupled to a proximal portion of the needle and disposed at least partially within the elongate body member for moving the needle between the first and second openings. The needle includes means for penetrating tissue and means for capturing and pulling a suture from the second opening.

In yet another aspect, the invention relates to a suturing instrument including an elongate body member including a distal portion defining a first opening and a second opening that opposes the first opening, a needle at least partially disposed within the elongate body member, and a needle deployment mechanism coupled to a proximal portion of the needle and disposed at least partially within the elongate body member for moving the needle between the first and second openings. The needle includes a hook-shaped distal portion for pulling a suture from the second opening and a tissue-penetrating tip distal of the hook-shaped distal portion. In one embodiment, the needle includes a latch movable between a first position in which the hook-shaped distal portion opens as the needle exits the first opening and a second position in which the hook-shaped distal portion closes as the needle exits the second opening with the suture, thereby capturing the suture in the hook-shaped distal portion of the needle.

In various embodiments of the foregoing aspects of the invention, the body member includes a protuberance disposed on an internal surface of the first opening. The protuberance acts to open the hook-shaped distal portion of the needle by moving the latch to the first position. The body member can include a protuberance disposed on an internal surface of the second opening. The protuberance acts to close the hook-shaped distal portion of the needle by moving the latch to the second position. The body member can also include a flexible tubular member disposed distal of the protuberance. The flexible tubular member holds a suture in place. In one embodiment, the flexible tubular member is a spring. The flexible tubular member can define a first lumen and the distal portion of the suturing instrument can define a second lumen generally axially aligned with the first lumen. In addition, the distal portion of the suturing instrument can include a slot in communication with the first lumen and the second lumen.

In some embodiments of the suturing instrument, the latch is pivotably coupled to the needle, in others the latch is slidably disposed on the needle. In one embodiment, the distal portion of the suturing instrument has a generally C-shaped or circular profile that defines an opening for receiving tissue. The needle can be substantially straight or curved. Where the needle is curved, the latch can be disposed on an inside diameter of the needle or an outside diameter of the needle. In additional embodiments, the elongate body member can include one or more bends. The suturing instrument can be adapted to access remote organs or tissue within a body. The distal portion of the elongate body member may be rotatable relative to the remainder of the elongate body member. Further, the suturing instrument can include a handle disposed opposite the distal portion of the elongate body member. The handle can at least partially house the needle deployment mechanism. The suturing instrument can also include a suture disposed in the second opening.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1A is a schematic plan view of one embodiment of a suturing instrument in accordance with the invention;

FIGS. 1B and 1C are schematic cross-sectional views of the proximal and distal portions of the suturing instrument of FIG. 1A;

FIGS. 2C, 2F, and 2I are enlarged schematic top views of the distal portion of the suturing instrument of FIG. 1A in various operational phases;

FIGS. 8A–8F are schematic perspective views of another alternative needle embodiment.

DESCRIPTION

Embodiments of the present invention are described below. It is, however, expressly noted that the present invention is not limited to these embodiments, but rather the intention is that variations, modifications, and equivalents that are apparent to the person skilled in the art are also included.

Figure 1D:
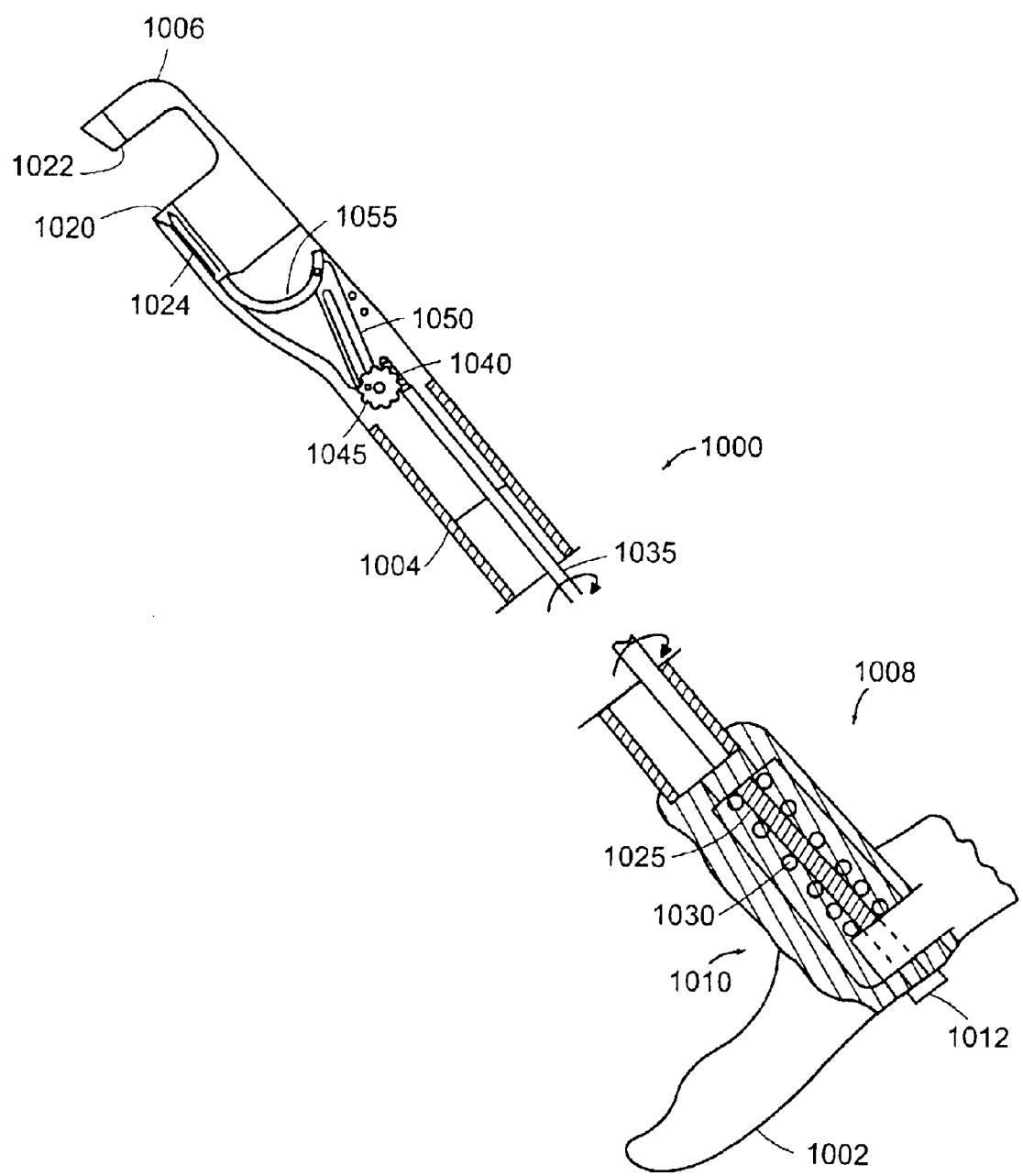
FIG. 1D is a schematic cross-sectional view of an alternative embodiment of the suturing instrument of FIG. 1A.

A suturing instrument according to the invention can be used, for example, to access areas within the human body to ligate, fixate, or approximate tissue. The suturing instrument can throw one or more stitches intercorporeally. FIG. 1A illustrates the general structure of one embodiment of the present invention. FIG. 1A depicts a suturing instrument 100 including a handle 102, an elongate body member 104, and a needle deployment mechanism 110. The suturing instrument 100 has a distal portion 106 and a proximal portion 108. The elongate body member 104 is mechanically coupled to the handle 102 at the proximal portion 108 and the suturing components are housed in the distal portion 106 of the suturing instrument 100.

The handle 102 could take a variety of forms, for example, the handle 102 could be one of the types used with Boston Scientific Corporation suturing systems, in particular the Capio® Push & Catch suturing system. Generally, the needle deployment mechanism 110 extends longitudinally through the elongate body member 104 to the distal portion 106 of the suturing instrument 100, where the needle deployment mechanism 110 is coupled to a needle. The needle deployment mechanism 110 moves the needle between a retracted position and a deployed position. One example of the needle deployment mechanism 110 is shown in greater detail in FIGS. 1B and 1C.

FIGS. 1B and 1C are cross-sectional views of the proximal portion 108 of the suturing instrument 100 (FIG. 1B) and the distal portion 106 of the suturing instrument 100 (FIG. 1C). FIG. 1B depicts the suturing instrument 100 including the handle 102, the elongate body member 104, and the needle deployment mechanism 110. The needle deployment mechanism 110 includes a button 117, a shaft 116, a bearing 118, a button end 119, and a hole 121. The bearing 118 rides along a cylindrical surface 105 that is formed by the inside diameter of the elongate body member 104. A wireform 103 is inserted into the hole 121, coupling it to the actuator button 117. A spring 115 encircles the wireform 103, abuts the button end 119, and is compressed between the button end 119 and a spring washer 113. The spring washer 113 is seated upon a center tube 107. The center tube 107 is housed by the cylindrical surface 105 and is constrained at the distal portion 106. A pusher wire 111 is attached to the wireform 103 by means of a weld, a coupling, adhesive or other means and is slidably disposed within a guidance sleeve 109, the sleeve 109 being disposed within a cylindrical surface 123 formed by the inside diameter of the center tube 107. In one embodiment, the pusher wire 111 is constructed of nitinol. Nitinol is a nickel-titanium alloy so chosen for its combination of properties that allow for bendability and high column strength when constrained.

FIG. 1C is a detailed cross-sectional view of the distal portion 106 of the suturing instrument 100. The pusher wire 111 is attached by welding or other means to a coupling 150, which is slidably disposed within a track 152. The coupling 150 is attached to a carrier wire 154, which by virtue of its attachment to the coupling 150 is also slidably disposed within the track 152. The carrier wire 154 is mechanically coupled to the needle 124 by means of a weld, a coupling, adhesive, or other means. The coupling 150 abuts a backstop washer 156 that is slidably disposed about the pusher wire 111 and is contained within a pocket 160 that includes a back wall 162, against which the backstop washer 156 rests. The track 152 terminates distally in a pocket 164 that includes a wall 166. A downstop washer 158 is slidably disposed about the carrier wire 154 and constrained within the pocket 164.

In operation, the needle deployment mechanism 110 is actuated by pushing on the button 117, which via the attachment to the wireform 103 which is attached to the pusher wire 111, moves the coupling 150 along the track 152 concomitantly moving the carrier wire 154, which slidably moves the needle 124, thereby driving the needle 124 through tissue. As the pusher wire 111 responds to greater urging of the button 117, the coupling 150 reaches a point in its travel along the track 152 where it pushes the downstop washer 158 such that it abuts the wall 166 of the pocket 164. This action limits the outward travel of the carrier wire 154 to prevent overdriving and eliminate the possibility of expelling the needle 124 from the suturing instrument 100. As the button 117 is released, the spring 115 urges the button 117 proximally, moving the pusher wire 111, the coupling 150, and the carrier wire 154 proximally along with the button 117 to the retracted position.

In an alternative needle deployment mechanism 1010 (FIG. 1D), the button 1012 operates a drive screw 1025 and a compression spring 1030, which are housed in the proximal portion 1008 of the body 1004. The button 1012 is mechanically linked to the drive shaft 1035, which moves a gear drive 1040, which in turn drives a gear 1045. The gear 1045 is coupled to a link drive pin 1050, which is itself coupled to a needle pusher 1055. The needle pusher 1055 is in turn coupled to a needle 1024. The pusher 1055 advances the needle 1024 out of a needle exit port 1020 and into a needle receiving port 1022. The spring 1030 acts to retract the needle 1024 from the needle receiving port 1022 once the button 1012 is released.

In some embodiments, the suturing instrument 100 may include an optional articulation 114 disposed in the elongate body member 104 proximate the distal portion 106 (FIG. 1A). The articulation 114 facilitates the rotation and positioning of the distal portion 106 of the suturing instrument 100. In addition, the elongate body 104 can be substantially straight or may include one or more bends. The articulation 114 and/or bend(s) can facilitate access to deep and/or difficult to reach areas within the human body.

The suturing instrument's component materials should be biocompatable. For example, the handle 102, the elongate body member 104, and portions of the needle deployment mechanism may be fabricated from extruded, molded, or machined plastic material(s), such as polypropylene, polycarbonate, or glass-filled polycarbonate. Other components, for example the needle 124, may be made of stainless steel. Other suitable materials will be apparent to those skilled in the art. The type of material(s) used to form the suture is not critical to the present invention, as long as the material is biocompatible. The surgeon will select the length, diameter, and characteristics of the suture to suit a particular application. Additionally, the mechanical components and operation are similar in nature to those disclosed in U.S. Pat. Nos. 5,364,408 and 6,048,351, the disclosures of which are hereby incorporated herein by reference in their entireties.

Figure 2A:
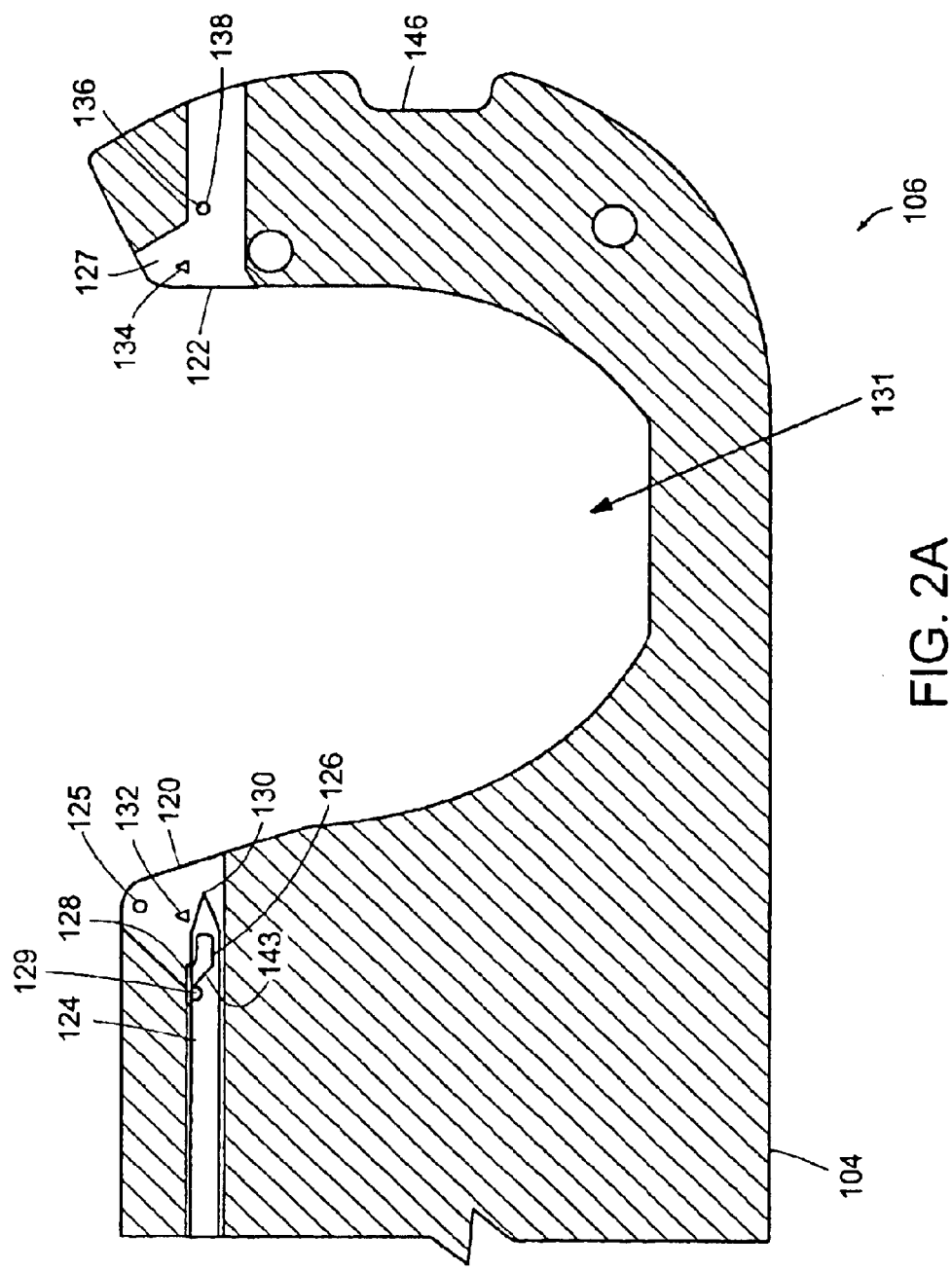
FIGS. 2A–2B, 2D–2E, and 2G–2H are enlarged cross-sectional side views of the distal portion of the suturing instrument of FIG. 1A in various operational phases.

FIGS. 2A–2I depict enlarged views of the distal portion 106 of the suturing instrument 100 and the suturing components during various phases of operation. FIG. 2A is an enlarged cross-sectional view of the distal portion 106 and depicts an elongate needle 124, a first opening or "needle exit port" 120, and a second opening or "needle receiving port" 122. The distal portion 106 has an essentially C-shaped profile; however, the profile can vary to suit a particular application, as long as the needle exit port 120 and the needle receiving port 122 are generally in opposition. In many instances, the open area 131 defined by the C-shaped profile receives the tissue to be sutured. The needle 124 includes a hook-shaped distal portion 126, a tip 130 disposed distally therefrom, and an optional latch 128. The tip 130 is configured to penetrate tissue and has an essentially conical shape; however, the shape can vary to suit a particular application and may include cutting edges. The hook-shaped distal portion 126 is disposed in a side of the needle 124 and the size and shape of the hook shape can be chosen to suit a particular application. Examples of different needles and hook-shaped distal portions are illustrated in FIGS. 7A–7C and 8A–8F. The latch 128 is pivotably coupled to the needle 124 and opens the hook-shaped distal portion 126 in a first position and closes the hook-shaped distal portion 126 in a second position. In the embodiment shown, the latch 128 is coupled to the needle 124 via a hinge 129. In the first position, the latch 128 is pivoted back over the body of the needle 124, thereby opening the hook-shaped distal portion 126. In an alternative embodiment, the latch 128 is slidably coupled to the needle 124. The needle exit port 120 includes a latch opener 132 disposed therein for actuating the latch 128. The needle receiving port 122 includes a latch closer 134 disposed therein for actuating the latch 128 and a suture holder 136 disposed distally from the latch closer 134.

Figure 2B:
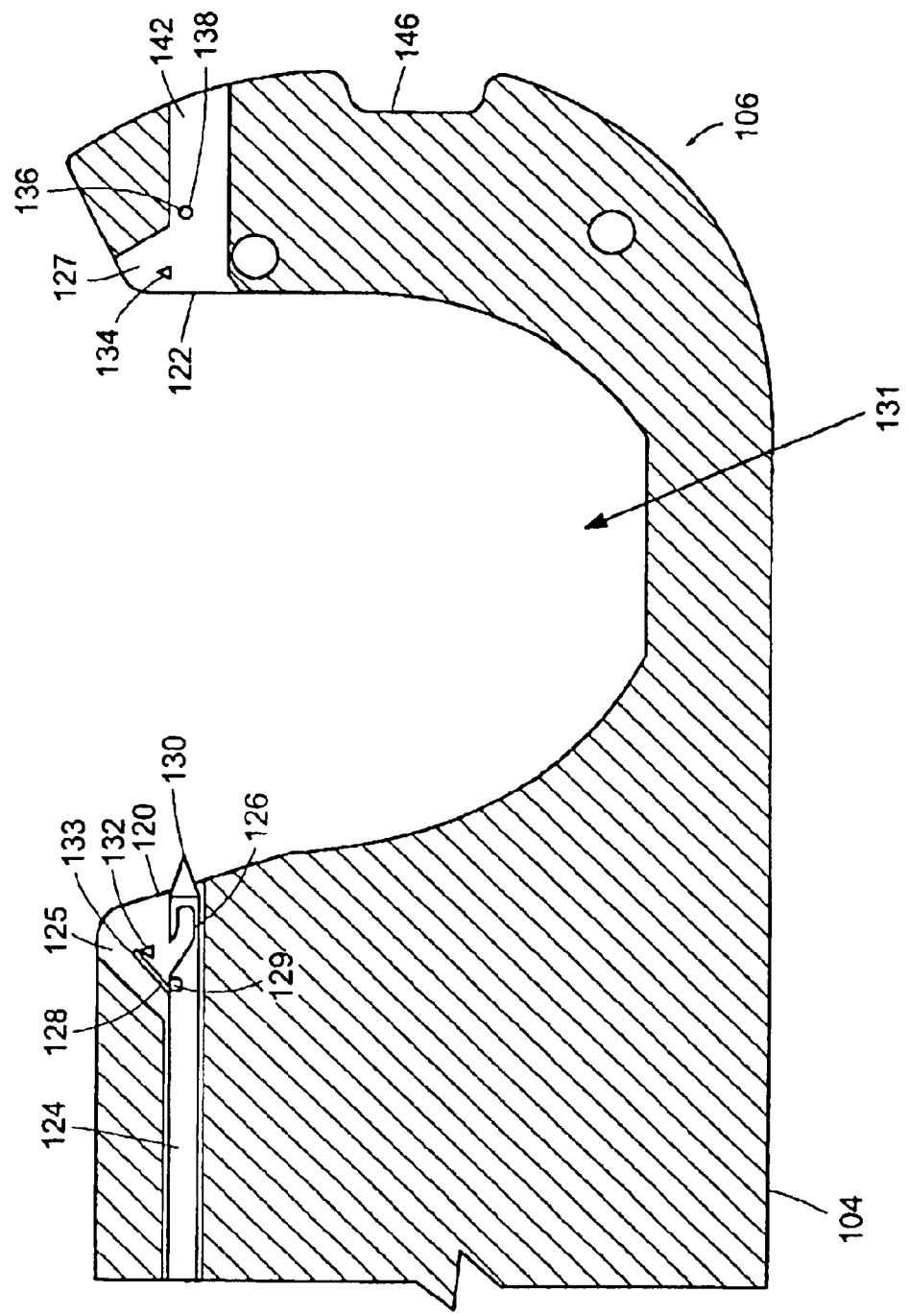

In FIG. 2A, the suturing instrument 100 is shown in a starting position with the needle 124 positioned within the needle exit port 120 proximal of the latch opener 132. In FIG. 2B, the needle 124 is advanced partially out of the needle exit port 120. As the needle 124 passes the latch opener 132, a leading edge 133 of the latch 128 contacts the latch opener 132, thereby pivoting the latch 128 up and opening the hook-shaped distal portion 126. Specifically, the latch 128 is caught and lifted by the latch opener 132. In one embodiment, the latch opener 132 extends the entire width of the needle exit port 120. As the needle 124 continues this forward movement, the latch 128 pivots at the hinge 129 approximately 180 degrees. The hook-shaped distal portion 126 is now completely open. The needle exit port 120 includes an open area 125 above the needle 124 that serves as clearance for the latch 128 as it pivots open. The needle 124 is free to continue past the latch opener 132, because the latch 128 can be either slightly recessed in the body of the needle 124 in the open position or the latch opener 132 can flex or rotate out of the path of the now open latch 128.

Figure 2C:
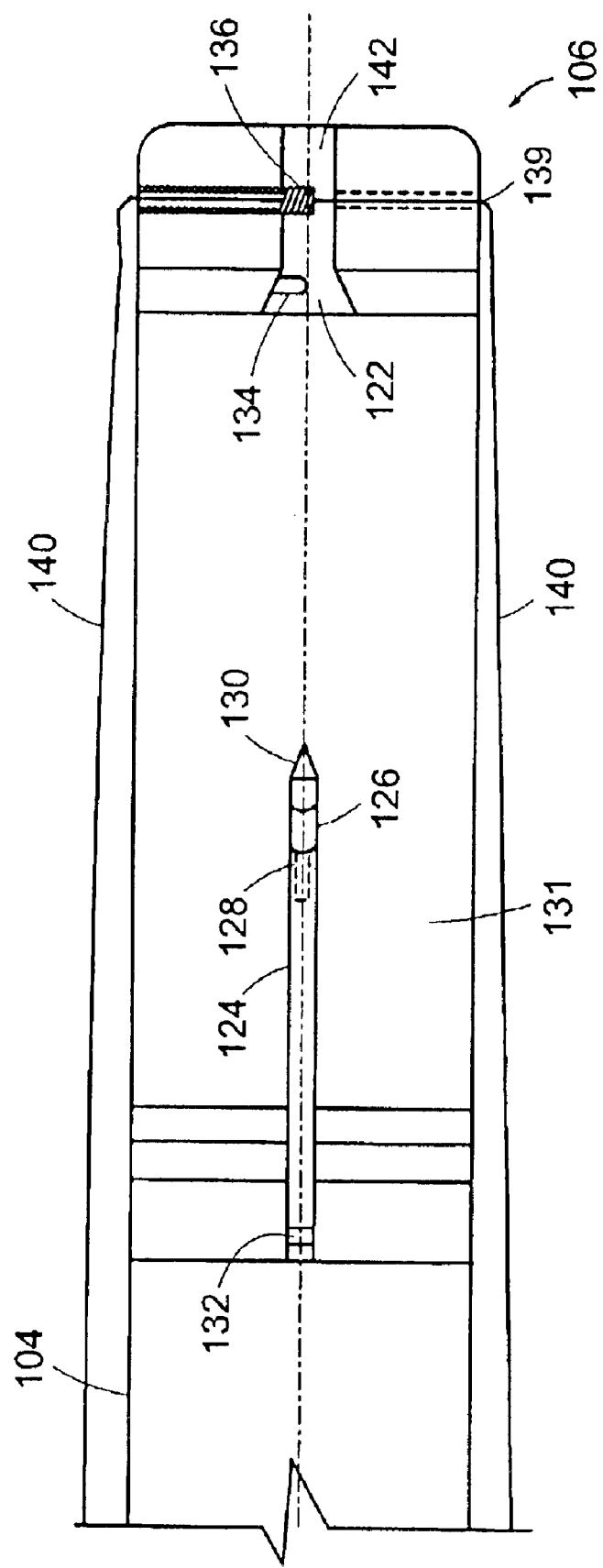

In FIG. 2C, the needle 124 is advanced approximately 50% of its full range. The latch 128 is pivoted back over the needle 124 and the hook-shaped distal portion 126 is fully exposed. While advancing the needle 124 through tissue, the tissue may prolapse into the hook-shaped distal portion 126; however, because the trailing edge 143 (FIG. 2A) of the hook-shaped distal portion 126 has no sharp edges, as shown in this embodiment, the tissue does not catch in the hook-shaped distal portion 126. In opposition to the needle exit port 120 is the needle receiving port 122. The needle receiving port 122 includes a latch closer 134 disposed on an interior wall thereof and extending approximately 50% of the width of the needle receiving port 122. The needle receiving port 122 also includes a suture holder 136 that extends approximately 50% of the width of the needle receiving port 122. The suture holder 136 is a generally flexible elongate member defining a lumen 138 extending therethrough (FIG. 2A). In the embodiment shown, the suture holder 136 is a spring; however, other flexible tubular structures may be used, for example, a nitinol tube. In operation, the suture holder 136 has one or more sutures 140 threaded through the lumen 138. Further, the suture 140 runs through a second lumen 139 disposed within the distal portion 106 of the suturing instrument 100 and generally axially aligned with the lumen 138 in the suture holder 136, thereby forming a suture bridge across the width of the needle receiving port 122. Typically, the suture 140 is threaded through the suture holder 136 and the second lumen 139 and the ends of the suture 140 are secured at or about the proximal portion 108 of the suturing instrument 100.

Figure 2D:
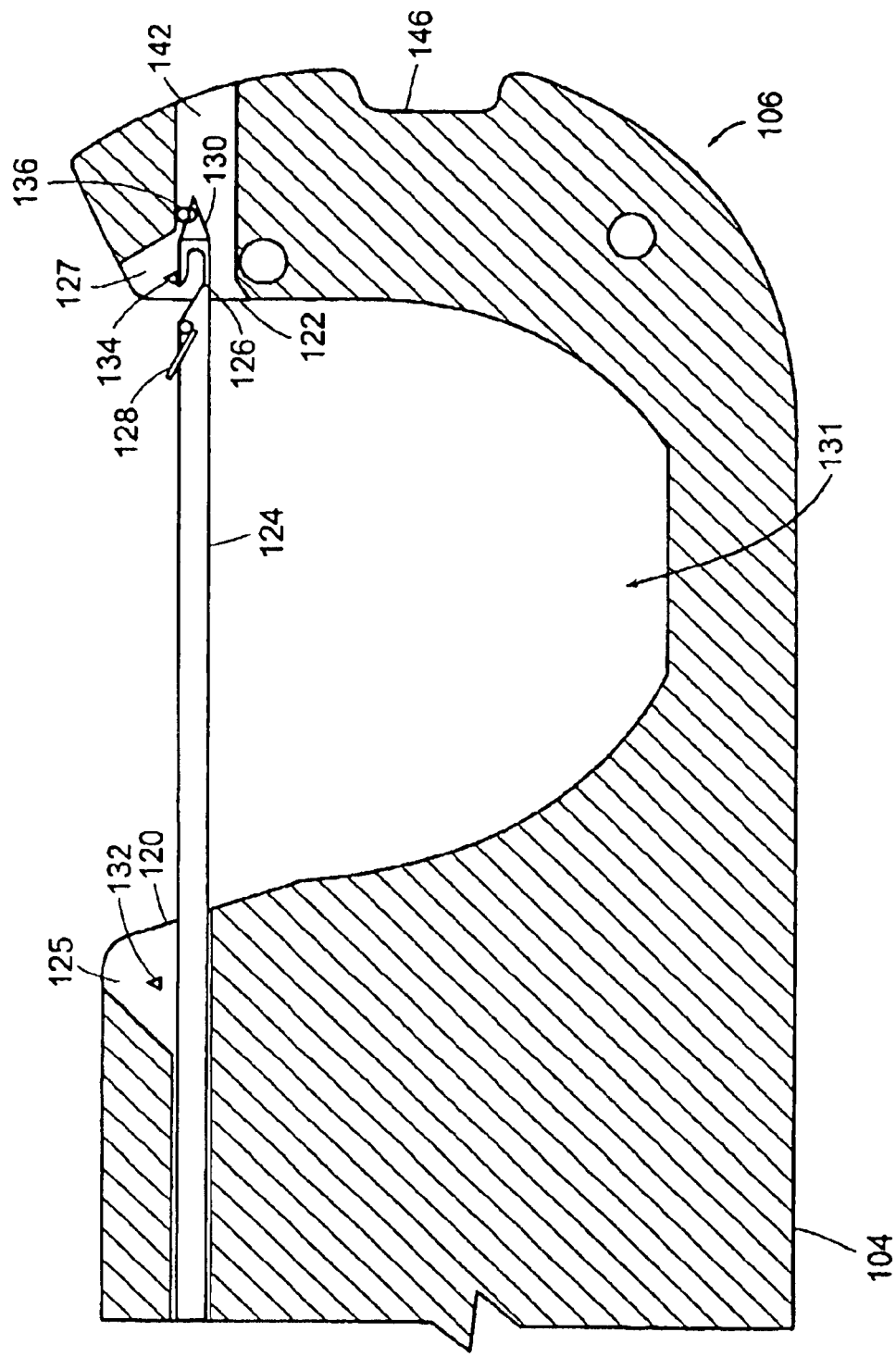
Figure 2E:
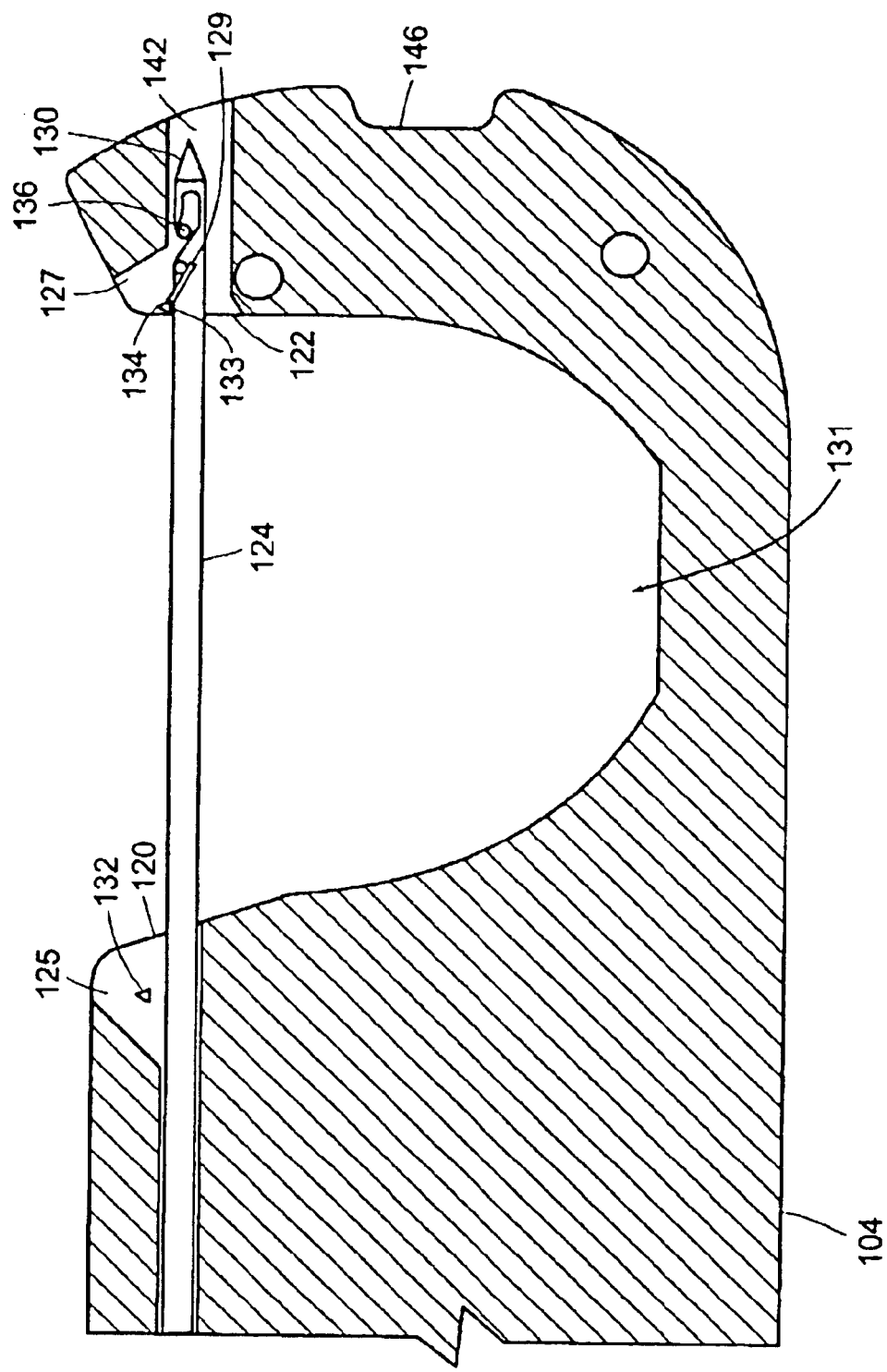
Figure 2F:
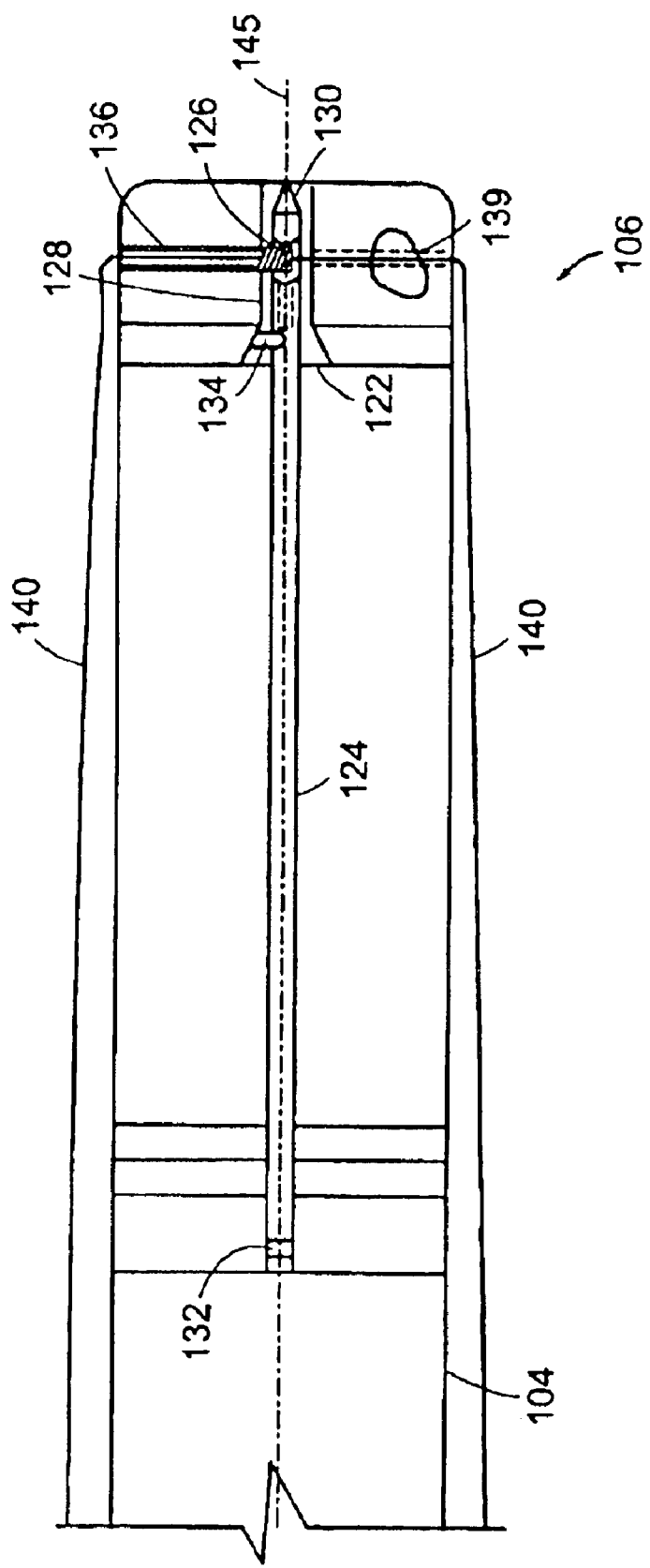

FIG. 2D depicts the needle 124 entering the funnel-shaped opening of the needle receiving port 122. The needle 124 advances past the latch closer 134 and contacts the suture holder 136. The suture holder 136 flexes in response to the force of the advancing needle 124 and is deflected upward to allow the needle tip 130 to pass the suture holder 136. The suture holder 136 helps to protect the suture 140 as the needle 124 passes. As can be seen in FIG. 2E, the suture holder 136 flexes back to its original position after the needle tip 130 advances past the suture holder 136 and the suture holder 136 and suture 140 drop into the hook-shaped distal portion 126. In this position, the suture 140 is captured within the hook-shaped distal portion 126 (FIG. 2F). As can be seen in FIG. 2F, the suture holder 136 extends past the centerline 145 of the needle receiving port 122; however, in other embodiments, the suture holder 136 extends about or less than the distance to the centerline 145.

Figure 2G:
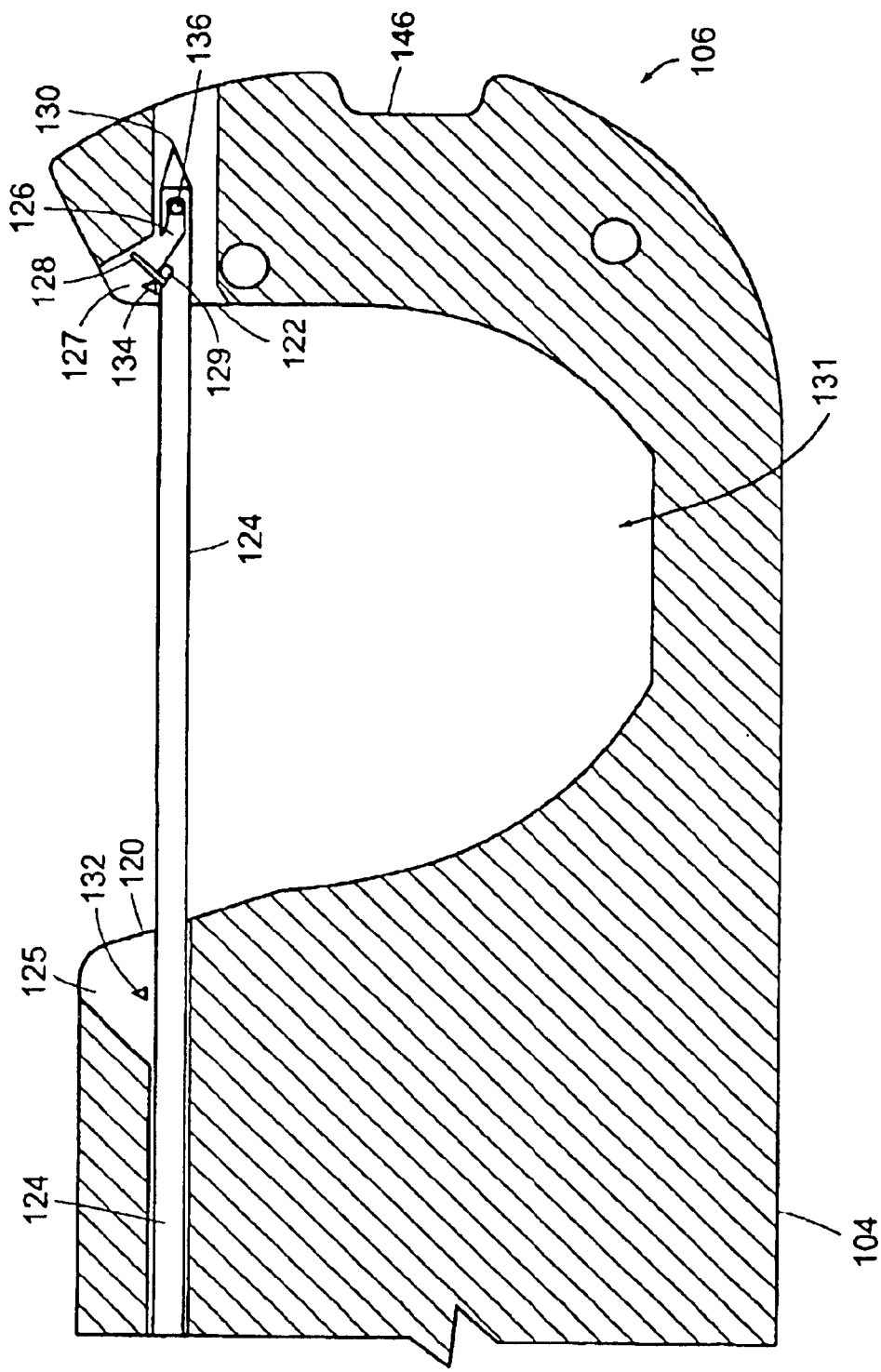

In FIG. 2G, the needle 124 is partially retracted from the needle receiving port 122. The needle 124 flexes the suture holder 136 out of the hook-shaped distal portion 126, but holds onto the suture 140 as the needle 124 moves past the suture holder 136. At approximately the same time, the leading edge 133 of the latch 128 engages the latch closer 134 and begins pivoting back to the closed position over the hook-shaped distal portion 126. As the needle 124 continues to retract out of the needle receiving port 122 (FIGS. 2H and 2I), the latch 128 is fully pivoted to the second (or closed) position to capture the suture 140 within the hook-shaped distal portion 126. The needle receiving port 122 includes an open area 127 above the needle 124 that acts as clearance for the latch 128 as it pivots to the closed position. In addition to securing the suture 140 within the hook-shaped distal portion 126, the closed latch 128 prevents tissue from prolapsing into the hook-shaped distal portion 126, where it may become caught and/or torn by the hook-shaped distal portion 126; however, in embodiments without a latch 128, the size and shape of the hook-shaped distal portion 126 can be chosen to reduce or eliminate the possibility of tissue damage when retracting the needle 124.

Figure 2H:
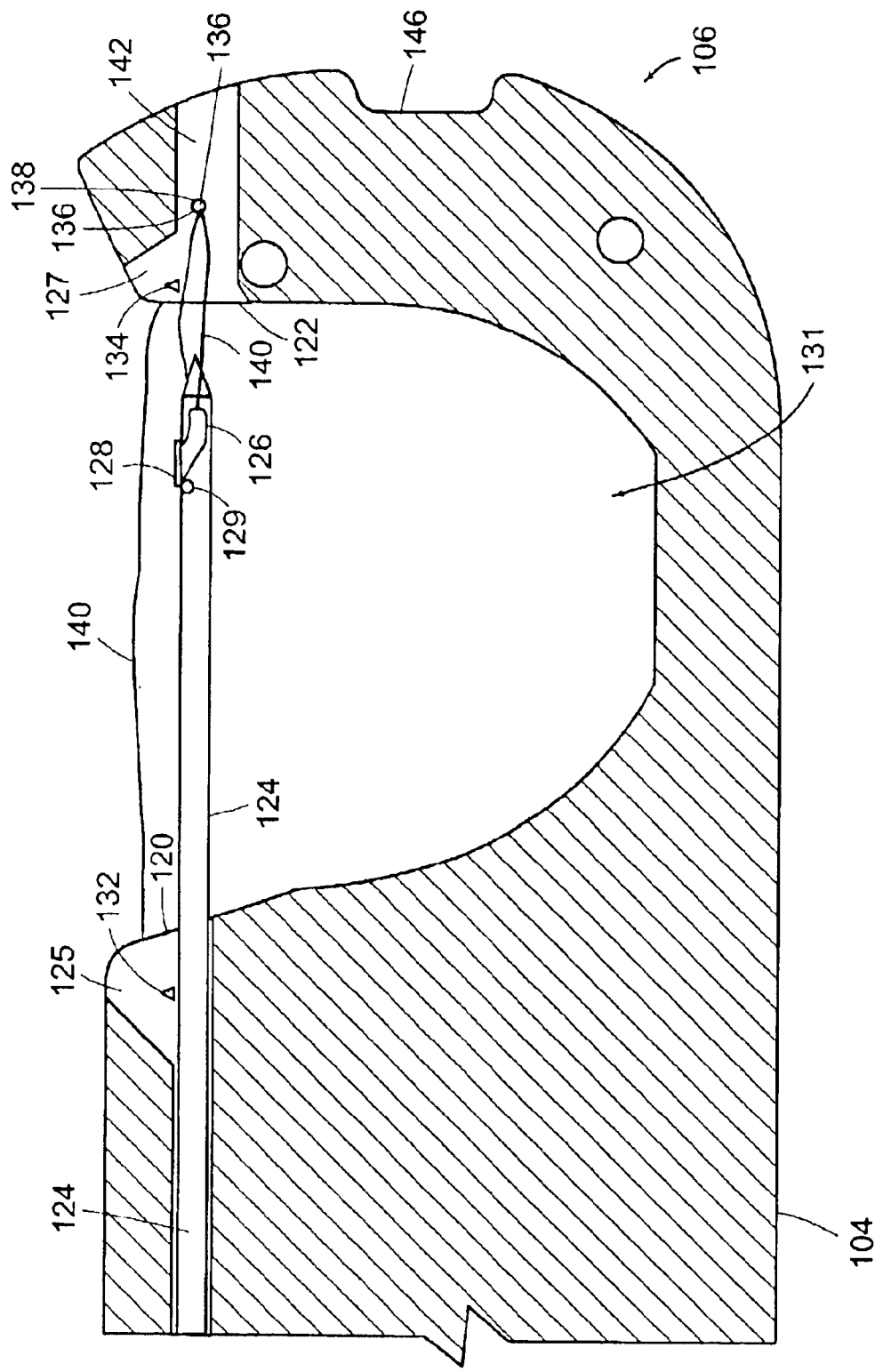
Figure 21:
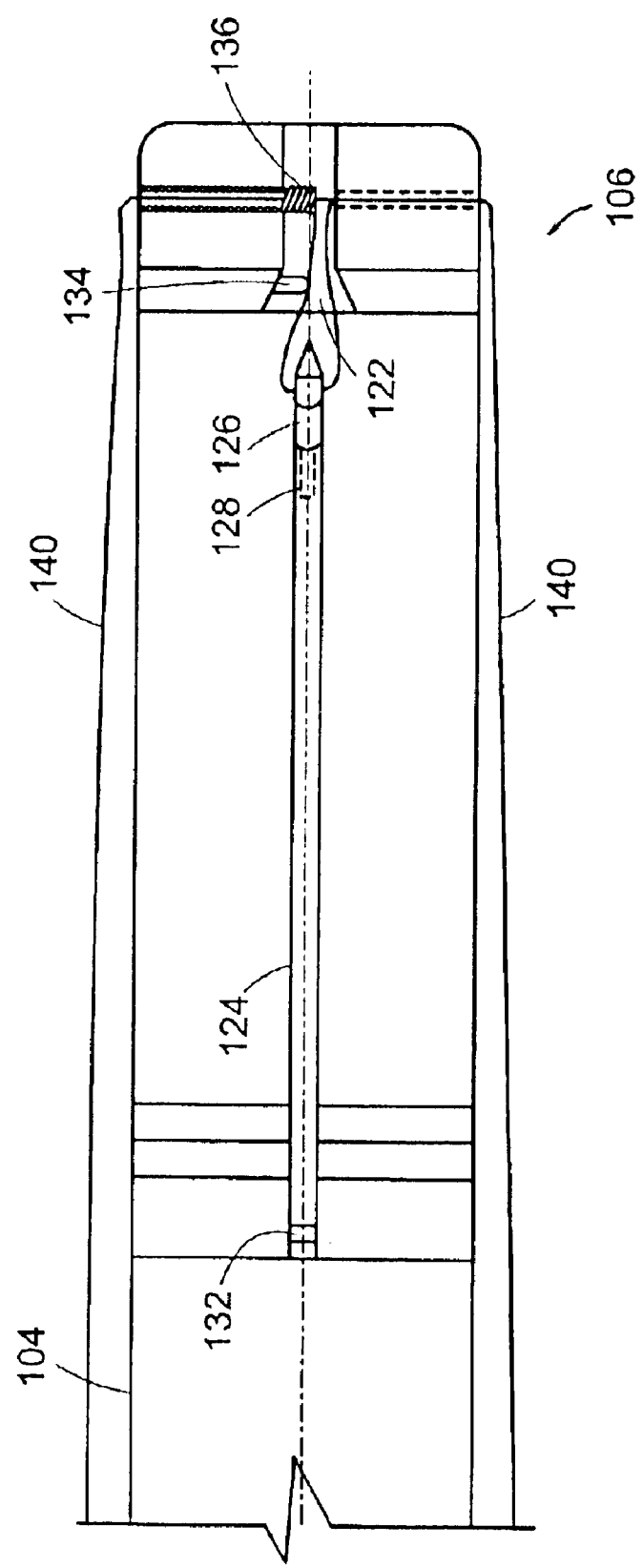

As shown in FIGS. 2H and 2I, the needle 124 is retracted through the open area 131 (and tissue if the device is so positioned) pulling the suture 140 through the open area 131 and/or tissue. After the needle 124 is fully retracted into the needle exit port 120, the suturing instrument 100 can be removed and the suture 140 retrieved and secured. The suture 140 can be knotted internally or externally to the body. Also, the suturing instrument may include a knot pusher 146 disposed on its distal portion 106 to help position the knot relative to the tissue. Alternatively, the needle 124 can be advanced again to capture a second suture.

Figure 3A:
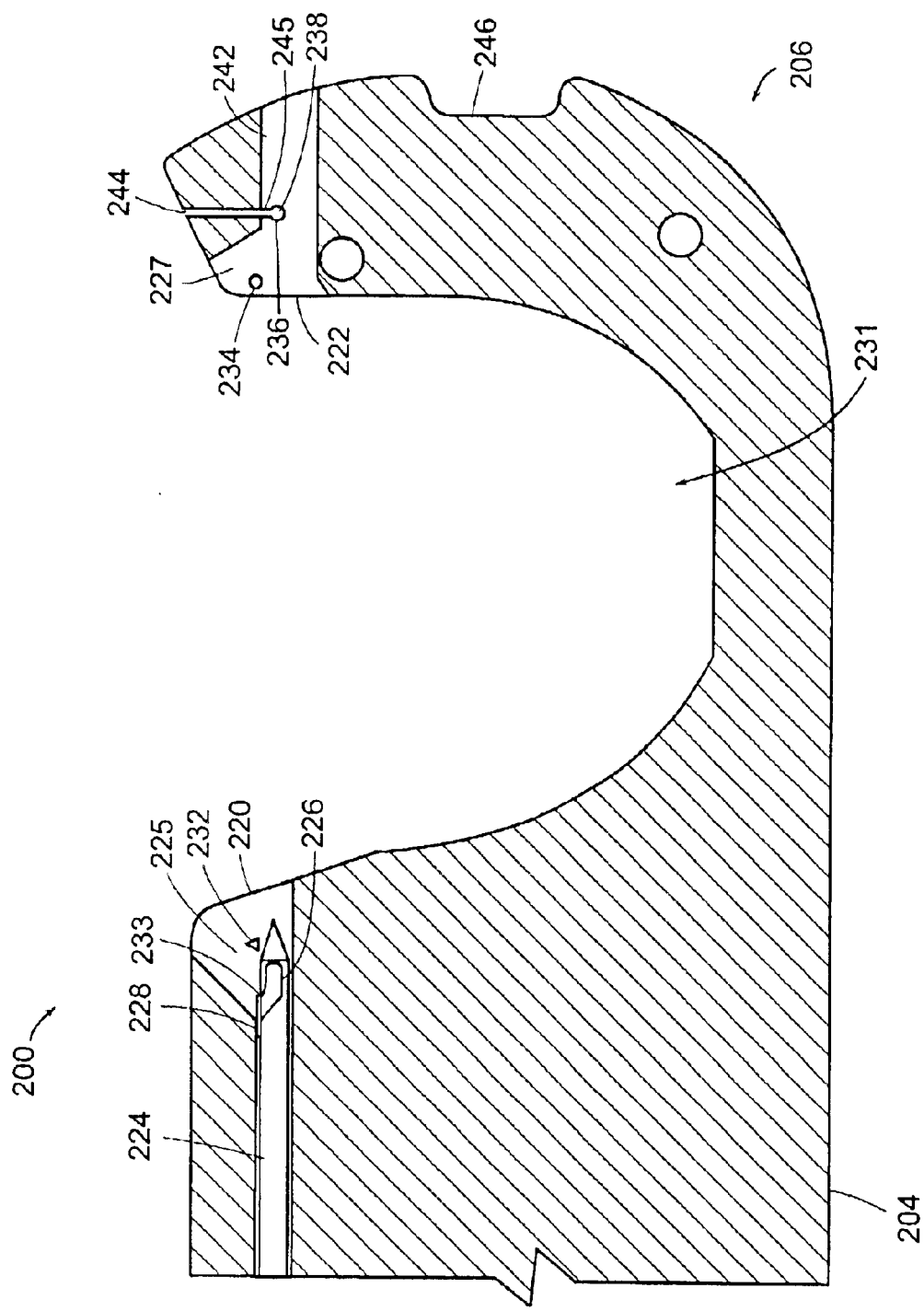
FIG. 3A is an enlarged cross-sectional side view of the distal portion of an alternative suturing instrument in accordance with the invention.
Figure 3B:
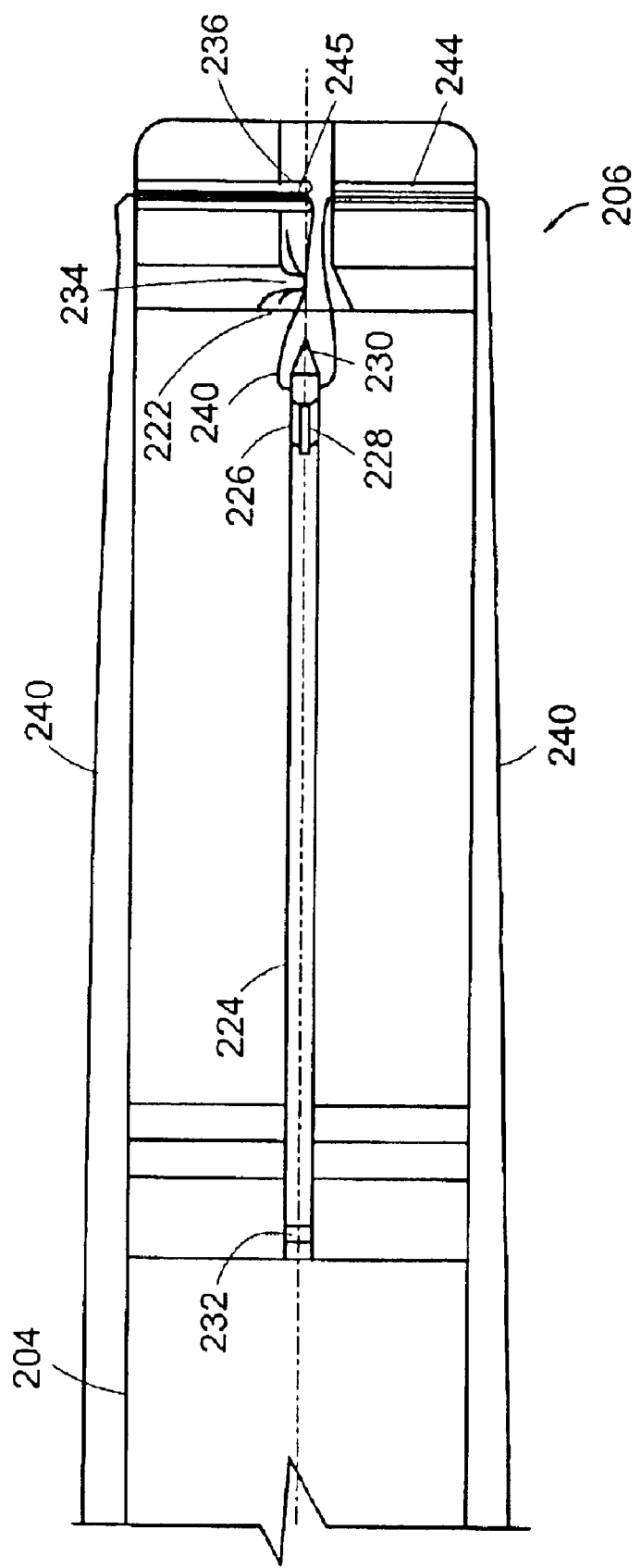
FIG. 3B is an enlarged top view of the distal portion of the suturing instrument of FIG. 3A.

FIGS. 3A and 3B depict an alternative embodiment of a suturing instrument 200 in accordance with the invention. The operation of the suturing instrument 200 is similar to that described with respect to FIGS. 2A–2I, but with several differences. The latch 228 is slidably disposed on the needle 224, as opposed to pivotably coupled to the needle 224. As the needle 224 advances out of the needle exit port 220, a leading edge 233 of the latch 228 engages a latch opener 232 disposed within the needle exit port 220. The latch opener 232 slides the latch 228 rearward into a first (or open) position, thereby exposing the hook-shaped distal portion 226. Once the latch 228 reaches the full open position, the needle 224 advances past the latch opener 232 by, for example, flexing the latch opener 232 out of alignment with the leading edge 233 of the latch 228.

The needle receiving port 222 includes a latch closer 234 and a suture holder 236. The latch closer 234 is a protuberance integrally formed with the opening of the needle receiving port 222 (FIG. 3B). The smooth contour of the latch closer 234 allows for easier passage of the suture 240 out of the needle receiving port 222. The suture holder 236 is a flexible tube, such as a nitinol tube. The distal portion 206 of the suturing instrument 200 includes a slot 244 vertically aligned with the suture holder 236. The suture holder 136 includes a slot 245 aligned with the slot 244 in the distal portion 206 of the instrument 200. The slots 244, 245 facilitate loading one or more sutures 240 into the suture holder 236 by just dropping the suture 240 into the slots 244, 245. As discussed hereinabove with respect to FIGS. 2D and 2E, the suture holder 236 flexes in response to the advancing needle 224, thereby allowing the needle 224 to capture the suture 240.

Figure 4A:
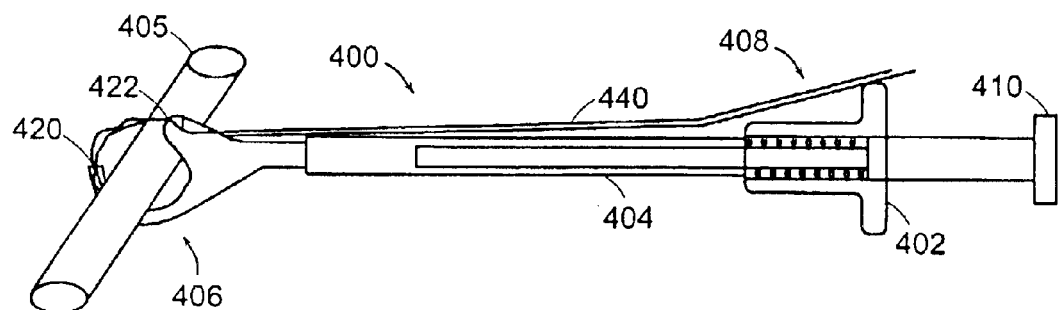
FIGS. 4A–4C are schematic representations of an alternative embodiment of a suturing instrument in accordance with the invention, as used in various applications.
Figure 4B:
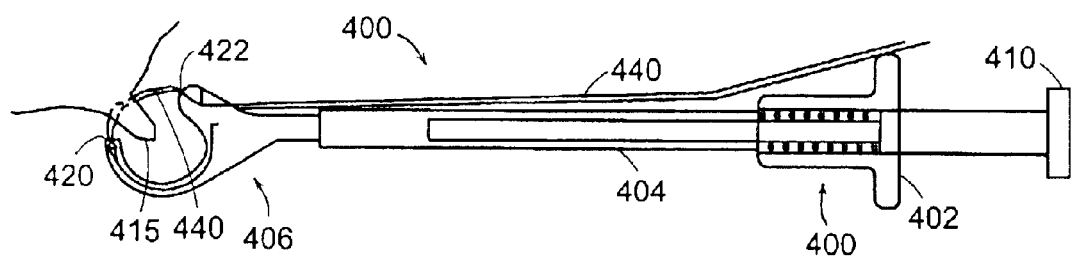
Figure 4C:
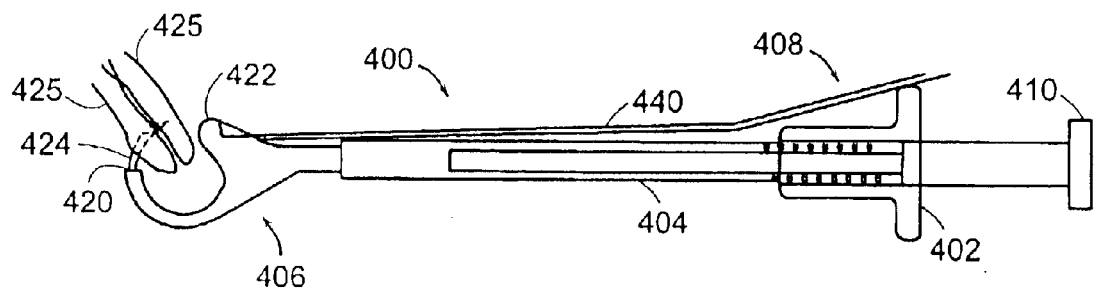

FIGS. 4A–4C depict various suturing procedures that can be performed with the suturing instrument 100 described hereinabove or an alternative embodiment of a suturing instrument 400 in accordance with the invention. The alternative embodiment of the suturing instrument 400 is similar in structure and operation to the suturing instrument 100 described hereinabove. The suturing instrument 400 includes a generally circular distal portion 406, which houses a curved needle 424. Other than the shape, the structure and operation of the needle 424 are similar to that described hereinabove. The hook-shaped distal portion 426 and latch 428 may be located on either the inside diameter or the outside diameter of the needle 424. The position of the latch opener 432 and the latch closer 434 within their respective ports will be adjusted as necessary to engage the latch 428. Alternatively, the needle 424 may not include a latch. The suturing instrument 400 depicted in FIGS. 4A–4C also differs from the previously described suturing instrument 100 with respect to the travel direction of the needle 424, 124. Needle 124 travels away from the proximal portion 108 of the suturing instrument 100 and needle 424 travels towards the proximal portion 408 of the suturing instrument 400.

In FIG. 4A, the suturing instrument 400 is being used to perform ligation, which is a procedure where a vessel, such as an artery, is closed off. The vessel 405 is positioned within the circular distal portion 406 of the instrument 400. The needle 424 is advanced out of the needle exit port 420, enters the needle receiving port 422, and is retracted back to the needle exit port 420 with the suture 440 captured within the hook-shaped distal portion 426. The instrument 400 can then be withdrawn leaving a length of suture 440 around the vessel 405, which can subsequently be tied off, thereby closing the vessel 405. In this procedure, the needle 424 carries the suture 440 around the vessel 405, but does not penetrate the vessel 405.

Figure 5A:
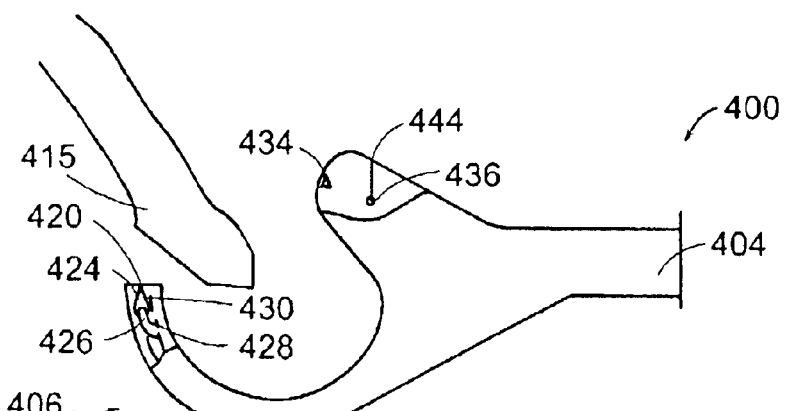
FIGS. 5A–5F are schematic representations of the method of using the suturing instrument of FIG. 4B.
Figure 5B:
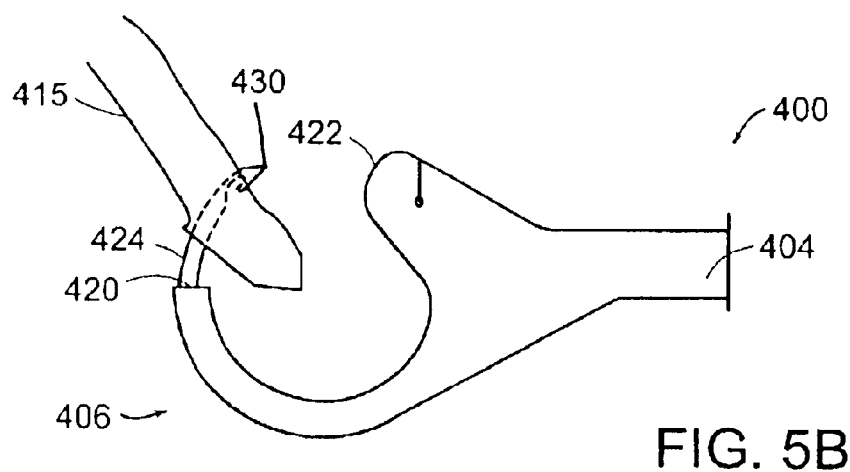
Figure 5C:
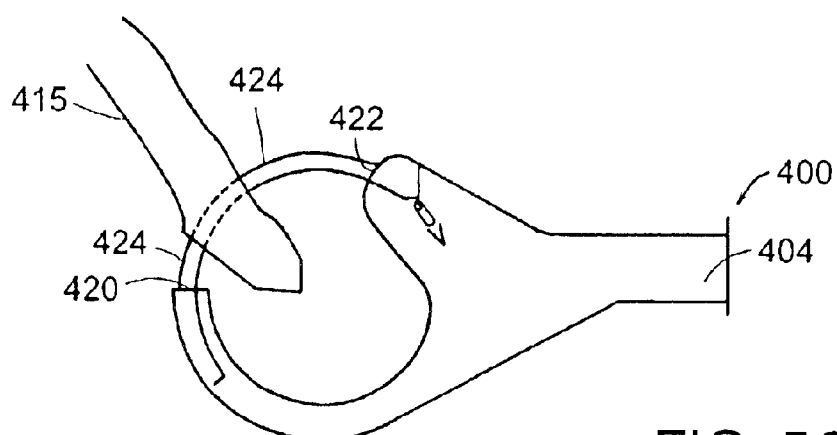
Figure 5E:
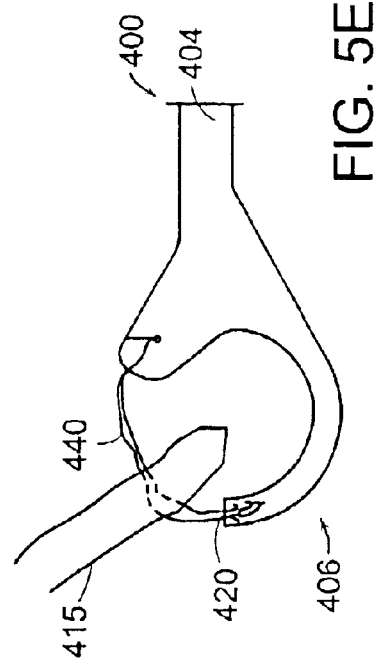
Figure 5D:
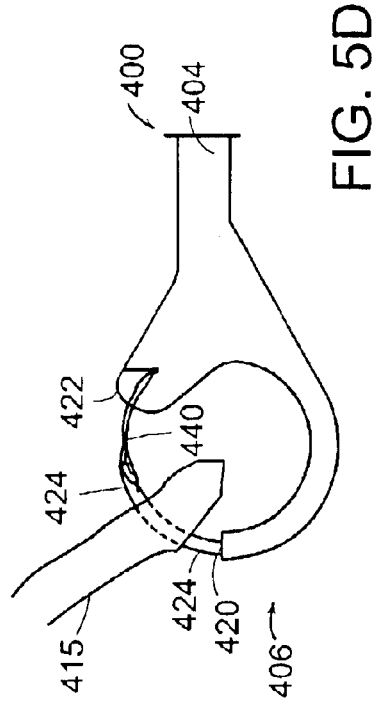
Figure 5F:
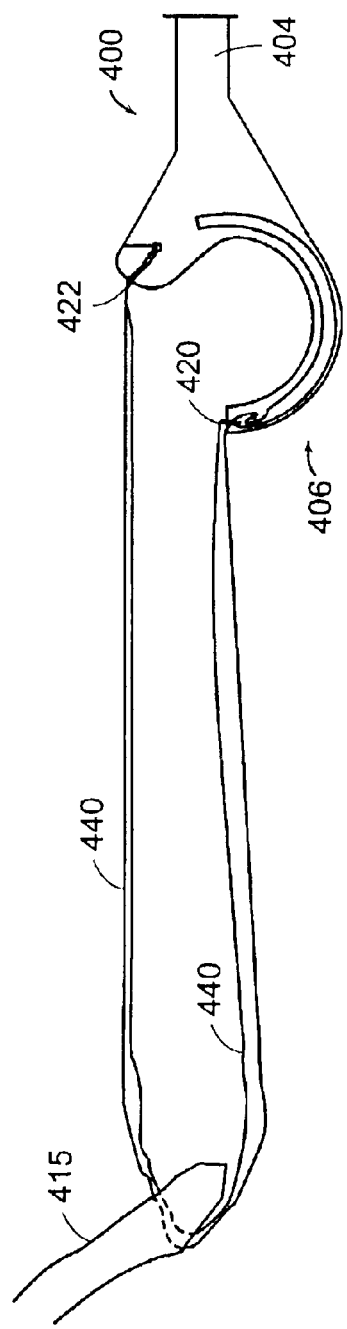

In FIG. 4B, the instrument 400 is being used to place a suture 440 through a single piece of tissue 415. As seen in greater detail in FIGS. 5A–5F, the needle 424 is driven through the tissue 415 until the needle 424 captures the suture 440 held within the needle receiving port 422 (FIGS. 5A–5C), as described above. Subsequently, the needle 424 is retracted back to the needle exit port 420, thereby pulling the suture 440 through the tissue 415 (FIGS. 5D and 5E). The needle 424 actually pulls a loop of suture 440 through the tissue 415, which results in two lengths of suture 440 through a common passage in the tissue 415. The instrument 400 can then be withdrawn leaving the two lengths of suture 440 through the tissue 415 (FIG. 5F), which subsequently can be secured to another structure.

In FIG. 4C, the instrument 400 is being used to approximate two pieces of tissue 425. The needle 424 is driven through the two pieces of tissue 425 until the needle 424 captures the suture 440 held within the needle receiving port 422. Subsequently, the needle 424 is retracted back to the needle exit port 420, thereby pulling the suture 440 through the tissue 425. The instrument 400 can then be withdrawn leaving a length of suture 440 through the tissue 425, which subsequently can be tied off to complete the approximation. In each preceding example, the needle 424 can be advanced a second time to pull an additional two lengths of suture 140 through or around the tissue 405, 410, 425.

Figure 6A:
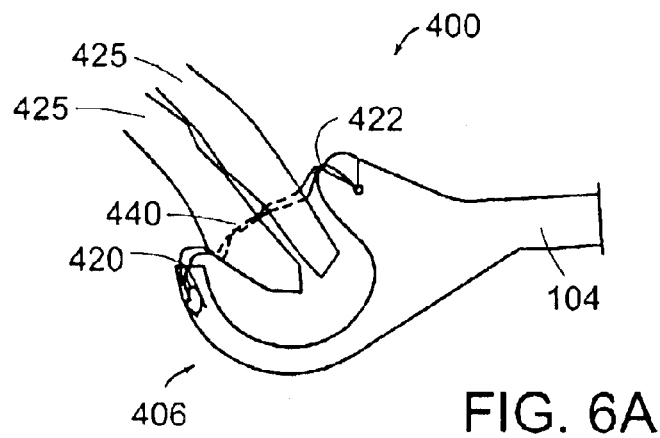
FIGS. 6A–6I are schematic representations of the method of using the suturing instrument of FIG. 4C to place additional stitches.
Figure 6B:
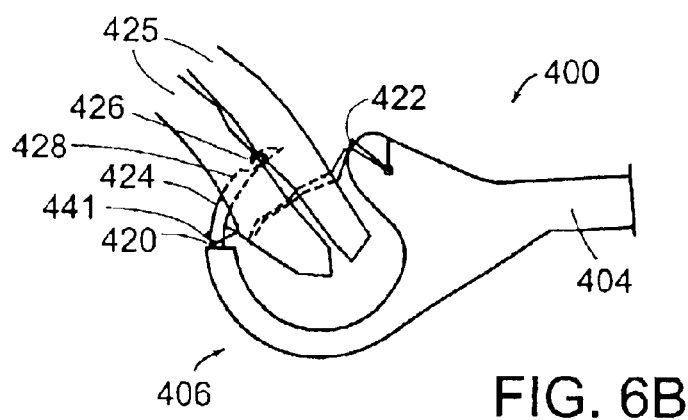
Figure 6C:
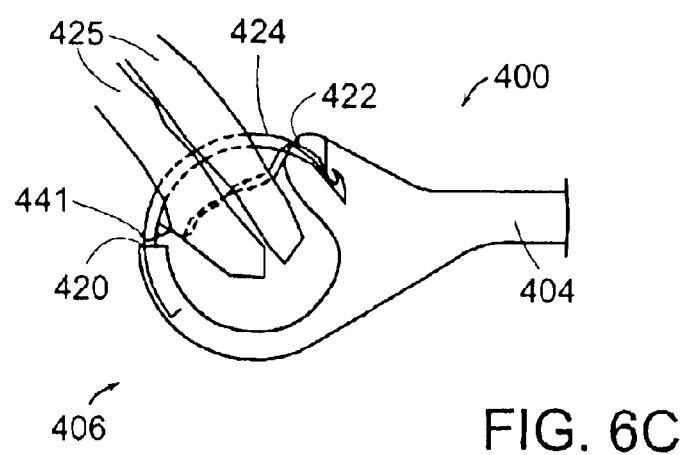
Figure 6D:
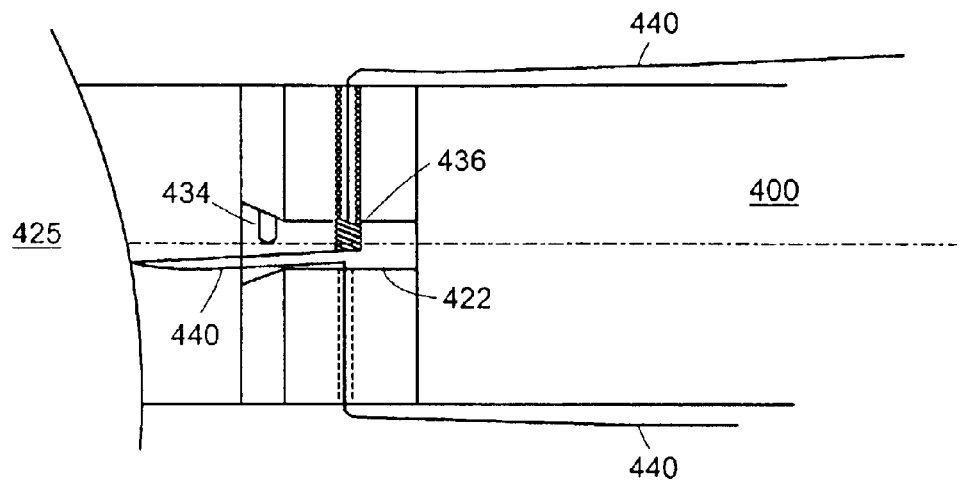
Figure 6E:
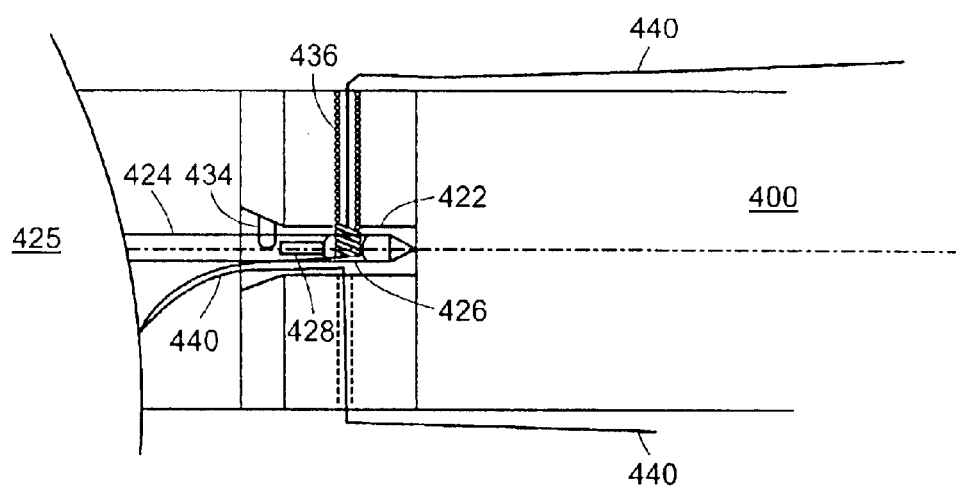

FIGS. 6A–6I depict the suturing instrument 400 of FIG. 4C being used to pass a second length of suture 440 through the tissue 425. FIGS. 6A–6C and 6F–6I are enlarged side views of the distal portion 406 of the suturing instrument 400, and FIGS. 6D and 6E are top views of the suturing instrument 400 shown in FIGS. 6B and 6D, respectively. In FIG. 6A, the suturing instrument 400 is moved to a position adjacent the tissue 425 that is offset from the first suture pass. In FIGS. 6B and 6C, the needle 424 is advanced through the tissue 425 until the needle 424 captures the suture 440 held within the suture holder 436 disposed within the needle receiving port 422. As can be seen in FIG. 6B, the suture is released from the hook-shaped distal portion 426 as the needle 424 is advanced and the latch 428 is opened. The needle 424 passes through a loop 441 in the suture 440 that was pulled through the tissue 425 by the first pass of the needle 424. In the embodiment shown, the hook-shaped distal portion 426 and latch 428 are disposed on the outside diameter of the needle 424.

Figure 6F:
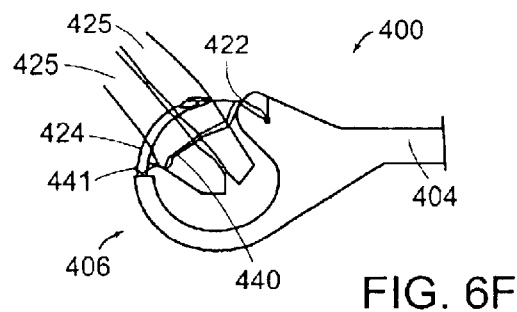
Figure 6G:
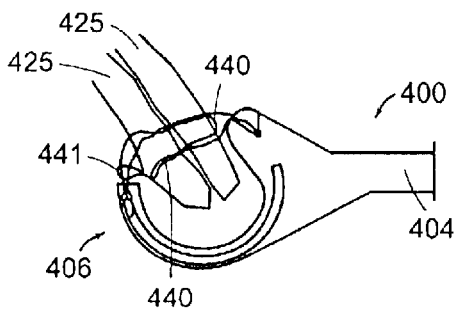
Figure 6H:
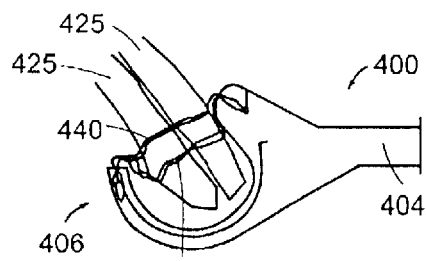
Figure 6I:
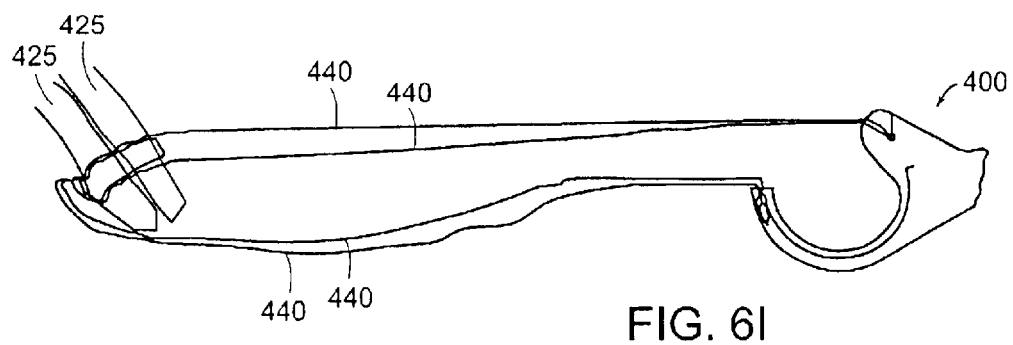

In FIG. 6D, the suture 440 is shown pulled from the needle receiving port 422. This length of suture 440 was pulled out during the first pass of the needle 424. As the needle 424 re-enters the needle receiving port 422 (FIG. 6E), the suture 440 is pushed aside by the needle 424 and the needle 424 deflects the suture holder 436 up and then into the hook-shaped distal portion 426, as discussed hereinabove with respect to FIGS. 2A–2I. As shown in FIGS. 6F–6H, the needle 424 is retracted from the needle receiving port 422 pulling another loop of suture 440 through the tissue 425. The second loop of suture 440 ends up within the first loop 441 (FIG. 6G). After the needle 424 is fully retracted into the needle exit port 420, the suturing instrument 400 can be removed (FIG. 6I) and the suture 440 retrieved and secured. The suture 440 can be knotted internally or externally to the body.

Figure 7A:
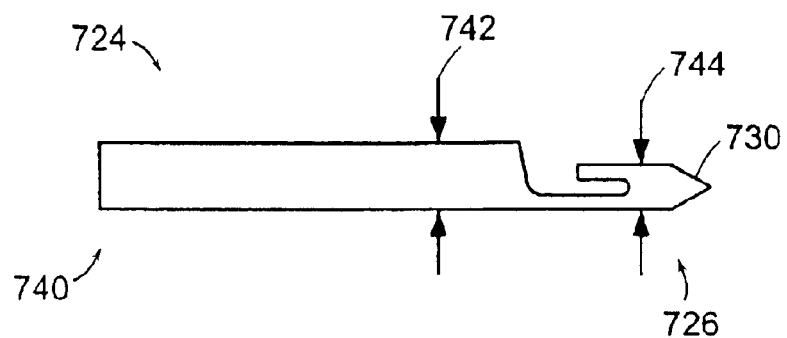
FIGS. 7A–7C are schematic side views of alternative needle embodiments.
Figure 7B:
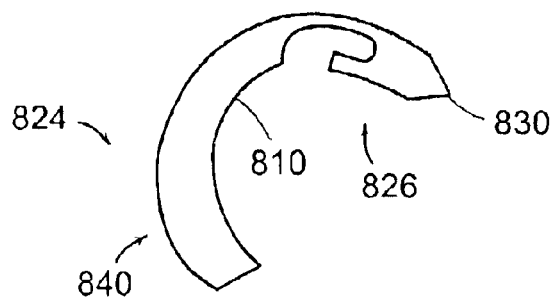
Figure 7C:
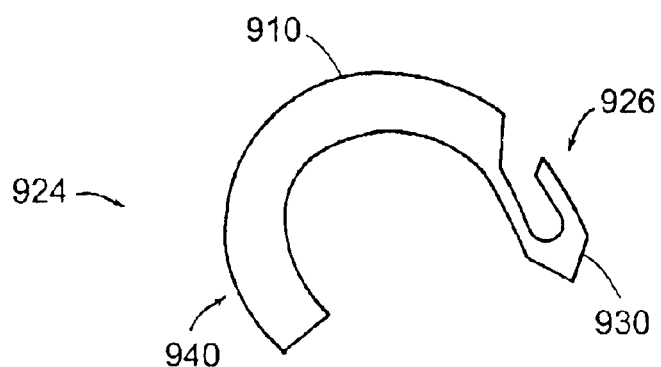

FIGS. 7A–7C depict various embodiments of needles that can be used in a suturing instrument in accordance with the invention. In FIG. 7A, the needle 724 is generally elongate and linear in shape and includes a proximal portion 740 and a hook-shaped distal portion 726. The diameter 744 of the hook-shaped distal portion 726 is smaller than the diameter 742 of the body of the needle 724. This reduction in diameter helps to prevent tissue from prolapsing into the hook-shaped distal portion 726 when retracting the needle 724 without a latch. In FIG. 7B, the needle 824 is generally curved and includes a proximal portion 840 and a hook-shaped distal portion 826. The hook-shaped distal portion 826 is oriented on the inside diameter 810 of the needle 824. The needle 924 shown in FIG. 7C is substantially the same as needle 824, except the hook-shaped distal portion 924 is oriented on the outside diameter 910 of the needle 924. In each of these embodiments, the proximal portion 740, 840, 940 can be mechanically coupled to the needle deployment mechanism 110.

Figure 8A:
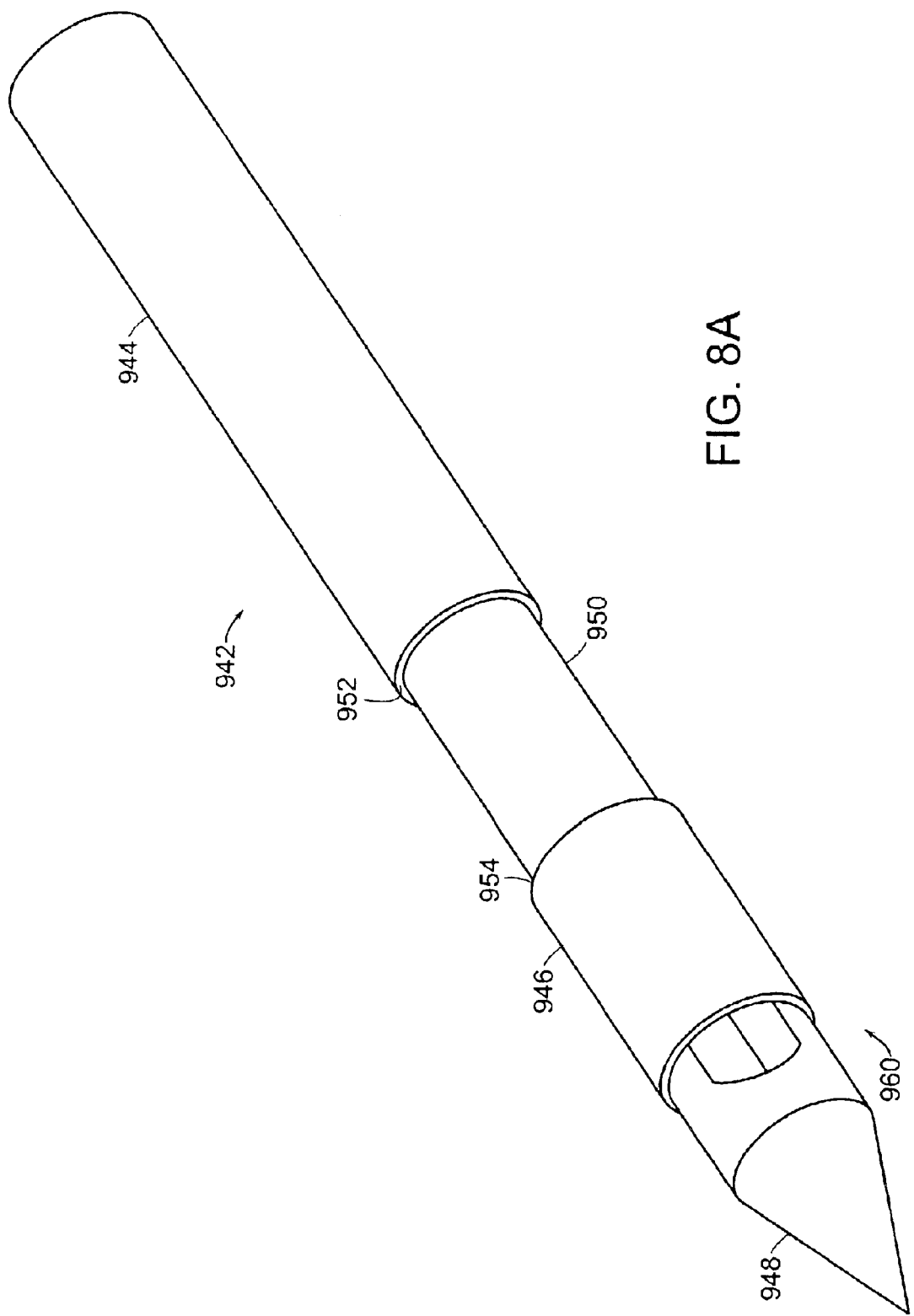

FIGS. 8A–8F depict another embodiment of a needle that can be used in a suturing instrument in accordance with the invention. The needle 942 is generally elongate and linear in shape and includes a body portion 950, a proximal tube portion 944, a hook-shaped distal portion 960 including a needle tip 948, and a latch 946. The proximal tube portion 944 includes a first stop edge 952 and the hook-shaped distal portion 960 includes a second stop edge 956 (FIG. 8B). The latch 946 includes a proximal edge 954 and a distal edge 964 and is slidably disposed about the body portion 950 to selectively expose (open) and cover (close) at least a portion of the hook-shaped distal portion 960.

Figure 8D:
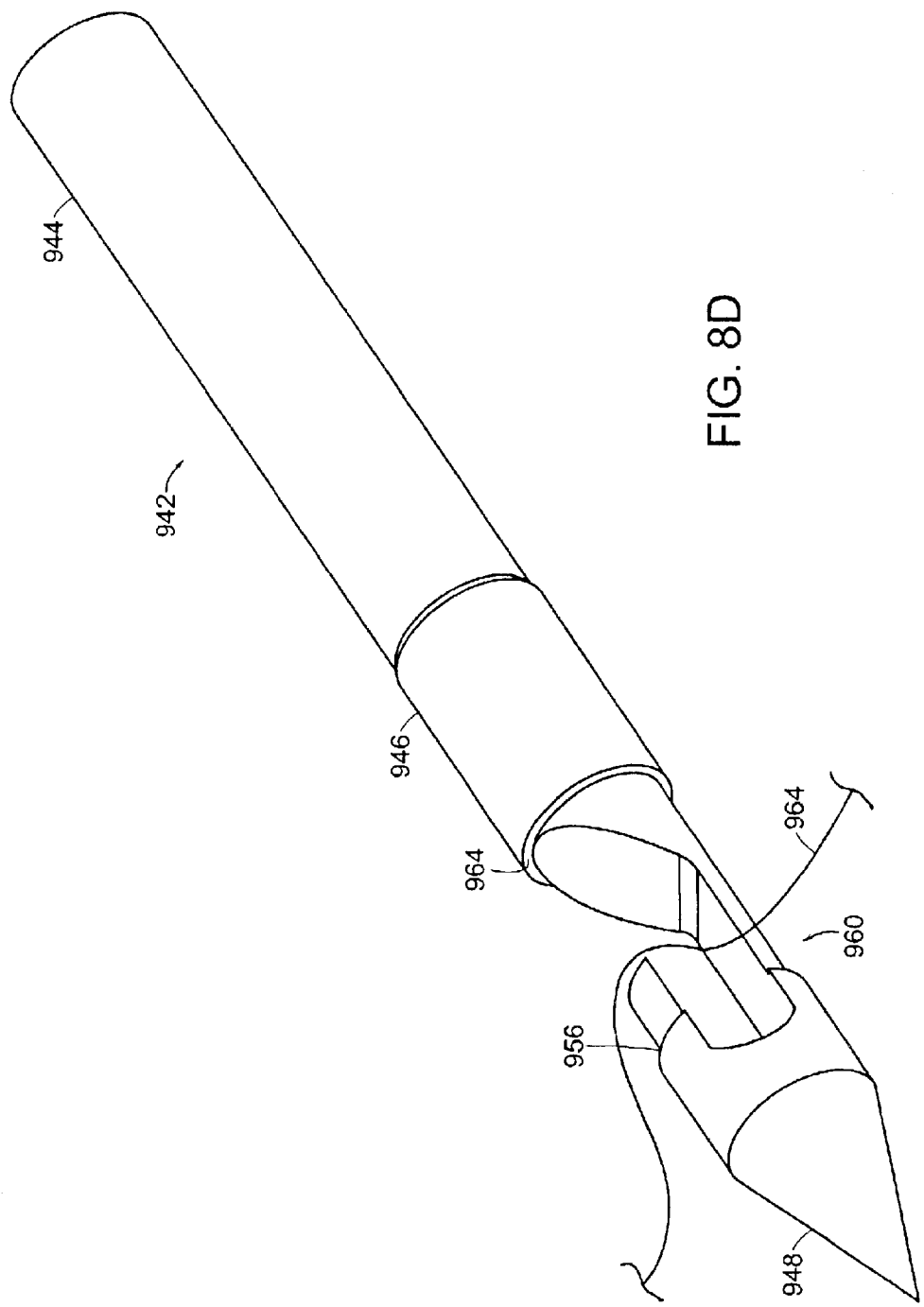
Figure 8E:
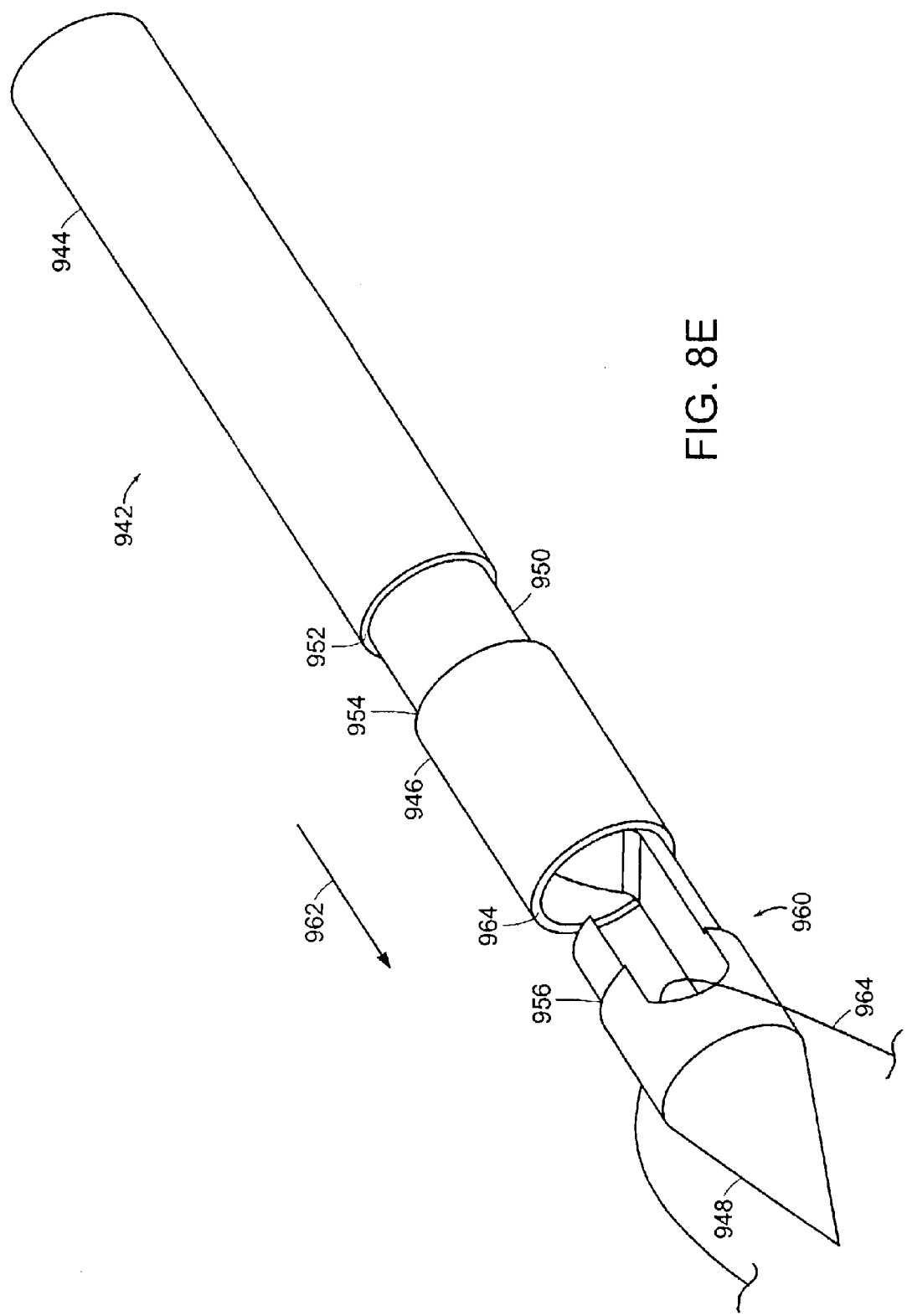

In operation, as a user pushes the needle 942 through a patient's tissue (by methods previously described), friction between the needle 942 and the tissue causes the latch 946 to slide over the body portion 950 in a direction indicated by arrow 958 until the proximal edge 954 contacts the first stop edge 952 (FIG. 8C). This results in the hook-shaped distal portion 960 being at least partially opened to capture a suture 968 (FIG. 8D). After the hook-shaped distal portion 960 captures the suture 968, the user retracts the needle 942 (by methods previously described). As the user retracts the needle 942, friction between the needle 942 and the tissue causes the latch 946 to slide over the body portion 950 in a direction indicated by arrow 962 until the proximal edge 954 contacts the second stop edge 956 (FIGS. 8E and 8F). This results in the hook-shaped distal portion 960 being at least partially closed by the latch 946. Covering the hook-shaped distal portion 960 with latch 946 helps to prevent tissue from prolapsing into the hook-shaped distal portion 960 when the user retracts the needle 942. Alternatively, the latch 946 can be opened and closed by contacting a latch opener and a latch closer as previously described and shown in FIGS. 2A–2I. The latch 946 has an outside diameter that is greater than any other outside diameter of the needle 942. As a result, only the latch 946 contacts the latch opener or latch closer when the needle 942 is advanced or retracted.

Other embodiments incorporating the concepts disclosed herein may be used without departing from the spirit and scope of the invention. The described embodiments are to be considered in all respects as only illustrative and not restrictive.

What is claimed is:

1. A suturing instrument comprising:
   an elongate body member including a distal portion defining a first opening and a second opening that opposes the first opening;
   a needle at least partially disposed within the elongate body member, the needle including a hook-shaped distal portion, a latch adapted to retain a suture within the hook-shaped distal portion, and a tissue-penetrating tip distal of the hook-shaped distal portion; and
   a needle deployment mechanism coupled to a proximal portion of the needle and disposed at least partially within the elongate body member for moving the needle between the first and second openings.

2. The suturing instrument of claim 1 wherein the latch is movable between a first position in which the hook-shaped distal portion is open and a second position in which the hook-shaped distal portion is closed.

3. The suturing instrument of claim 2 wherein the body member comprises a protuberance disposed on an internal surface of the first opening for moving the latch to the first position when the needle is moved from the first opening to the second opening.

4. The suturing instrument of claim 2 wherein the latch is pivotably coupled to the needle.

5. The suturing instrument of claim 2 wherein the body member comprises:

a protuberance disposed on an internal surface of the second opening for moving the latch to the second position when the needle is moved from the second opening to the first opening; and a flexible tubular member for holding a suture, the flexible tubular member disposed within the second opening and distal of the protuberance.

6. The suturing instrument of claim 5 wherein the flexible tubular member comprises a spring.

7. The suturing instrument of claim 5 wherein the flexible tubular member defines a first lumen and the distal portion of the suturing instrument defines a second lumen generally axially aligned with the first lumen.

8. The suturing instrument of claim 7 further comprising a slot defined by the distal portion of the suturing instrument, the slot in communication with the first lumen and the second lumen.

9. The suturing instrument of claim 2 wherein the latch is slidably disposed on the needle.

10. The suturing instrument of claim 1 wherein the needle is substantially straight.

11. The suturing instrument of claim 1 wherein the needle is curved.

12. The suturing instrument of claim 11 wherein the hook shaped distal portion is oriented on an inside diameter of the needle.

13. The suturing instrument of claim 1 further comprising a suture disposed within the second opening.

14. The suturing instrument of claim 1 wherein the elongate body member includes a bends.

15. The suturing instrument of claim 1 wherein the elongate body member includes two bends.

16. The suturing instrument of claim 1 further comprising a handle disposed opposite the distal portion of the elongate body member, the handle at least partially houses the needle deployment mechanism.

17. The suturing instrument of claim 1 wherein the distal portion of the elongate body member can rotate relative to a remainder of the elongate body member.

18. A suturing instrument comprising:

an elongate body member including a distal portion defining a first opening and a second opening that opposes the first opening;

a needle at least partially disposed within the elongate body member, the needle comprising:
    a body having a first diameter;
    a hook-shaped distal portion having a second diameter, the hook-shaped distal portion for capturing and pulling a suture from the second opening, wherein the second diameter is smaller than the first diameter;
    a tissue-penetrating tip distal of the hook-shaped distal portion;
    a latch movable between a first position in which the hook-shaped distal portion is opened as the needle exits the first opening and a second position in which the hook-shaped distal portion is closed as the needle exits the second opening with the suture, thereby capturing the suture in the hook-shaped distal portion of the needle; and a needle deployment mechanism coupled to a proximal portion of the needle and disposed at least partially within the elongate body member for moving the needle between the first opening and the second opening.

* * * * *